(12) United States Patent
Zhao et al.

(10) Patent No.: US 10,869,644 B2
(45) Date of Patent: Dec. 22, 2020

(54) METHOD AND SYSTEM FOR EXTRACTING LOWER LIMB VASCULATURE

(71) Applicant: SHANGHAI UNITED IMAGING HEALTHCARE CO., LTD., Shanghai (CN)

(72) Inventors: Peng Zhao, Shanghai (CN); Yufei Mao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 426 days.

(21) Appl. No.: 15/646,200

(22) Filed: Jul. 11, 2017

(65) Prior Publication Data

US 2018/0028137 A1 Feb. 1, 2018

Related U.S. Application Data

(63) Continuation of application No. PCT/CN2016/110071, filed on Dec. 15, 2016.

(30) Foreign Application Priority Data

Jul. 30, 2016 (CN) .......................... 2016 1 0617709

(51) Int. Cl.
*G06T 7/187* (2017.01)
*G06T 7/11* (2017.01)
(Continued)

(52) U.S. Cl.
CPC ................ *A61B 6/504* (2013.01); *A61B 6/03* (2013.01); *A61B 6/032* (2013.01); *A61B 6/5211* (2013.01);
(Continued)

(58) Field of Classification Search
CPC ........... A61B 6/504; A61B 6/03; A61B 6/032; A61B 6/5211; G06T 7/187; G06T 7/11;
(Continued)

(56) References Cited

U.S. PATENT DOCUMENTS 6,141,437 A * 10/2000 Xu ........................ G06T 7/0012
128/922
9,984,456 B2 * 5/2018 Wei ....................... G06T 7/0012
(Continued)

FOREIGN PATENT DOCUMENTS

| CN | 101551862 A | 10/2009 |
| CN | 101551906 A | 10/2009 |
| CN | 104978726 A | 10/2015 |

OTHER PUBLICATIONS

Search report in International Application No. PCT/CN2016/110071 dated May 12, 2017, 6 pages.
(Continued)

*Primary Examiner* — Bill Thomson
*Assistant Examiner* — Aminah Asghar
(74) *Attorney, Agent, or Firm* — Metis IP LLC

(57) ABSTRACT

The present disclosure relates to systems and methods for extracting a vessel of a lower limb. The methods may include obtaining an original image including a plurality of image data, in some embodiments, each of the plurality of image data may correspond to a pixel (or a voxel), the plurality of image data may include a target data set, the target data set may represent a first structure; extracting a first reference data set from the plurality of image data, in some embodiments, the first reference data set may include the target data set and a second reference data set, the second reference data set may include data of a second structure; extracting the second reference data set from the plurality of (Continued)

image data; and obtaining the target data set based on the first reference data set and the second reference data set.

17 Claims, 16 Drawing Sheets

(51) Int. Cl.
  *G06T 7/174* (2017.01)
  *A61B 6/00* (2006.01)
  *A61B 6/03* (2006.01)
(52) U.S. Cl.
  CPC ............... *G06T 7/11* (2017.01); *G06T 7/174* (2017.01); *G06T 7/187* (2017.01); *G06T 2207/10072* (2013.01); *G06T 2207/20112* (2013.01); *G06T 2207/30101* (2013.01)
(58) Field of Classification Search
  CPC . G06T 2207/30101; G06T 2207/20112; G06T 7/174; G06T 2207/10072
  See application file for complete search history.

(56) References Cited

U.S. PATENT DOCUMENTS

| | | | |
|---|---|---|---|
| 2003/0031351 A1* | 2/2003 | Yim ..................... | G06K 9/342 382/130 |
| 2005/0113679 A1* | 5/2005 | Suryanarayanan .... | A61B 6/481 600/425 |
| 2005/0163358 A1* | 7/2005 | Moeller ................. | G06K 9/342 382/128 |
| 2005/0228272 A1* | 10/2005 | Yu .......................... | A61B 6/466 600/425 |
| 2008/0094389 A1 | 4/2008 | Rouet et al. | |
| 2008/0118127 A1* | 5/2008 | Sirohey ................. | A61B 6/504 382/130 |
| 2010/0172556 A1* | 7/2010 | Cohen ................... | A61B 6/5217 382/128 |
| 2012/0014573 A1* | 1/2012 | Lautenschlager ..... | G06T 7/0012 382/128 |
| 2014/0316758 A1* | 10/2014 | Yagi ....................... | G16H 50/50 703/9 |
| 2014/0334678 A1* | 11/2014 | Ohishi ................... | G06T 7/0014 382/103 |
| 2015/0282890 A1* | 10/2015 | Cohen .................... | A61B 6/481 600/424 |
| 2016/0089010 A1 | 3/2016 | Aoyama | |
| 2016/0260212 A1* | 9/2016 | Ouji .......................... | G06T 7/20 |
| 2017/0042495 A1* | 2/2017 | Matsuzaki .............. | A61B 5/00 |
| 2017/0213344 A1* | 7/2017 | Hong .................... | G06K 9/0014 |

OTHER PUBLICATIONS

M. Freiman et al., Nearly automatic vessels segmentation using graph-based energy minimization, The Midas Journal, 8 Pages, 2009.

Hackjoon Shim et al., Partition-Based Extraction of Cerebral Arteries from CT Angiography with Emphasis on Adaptive Tracking, IPMI, LNCS 3565, pp. 357-368, 2005.

Olivier Cuisenaire et al., Fully automated segmentation of carotid and vertebral arteries from CTA, 11 Pages, 2008.

Pedro T. Vieco et al., Detection of circle of Willis aneurysms in patients with acute subarachnoid hemorrhage: a comparison of CT angiography and digital subtraction angiography, AJR 165 (2):425-430, 1995.

Tan, Yongqiang et al., Segmentation of lung lesions on CT scans using watershed, active contours, and Markov random field, Medical Physical, 40(4): 043502, 10 Pages, 2013.

* cited by examiner

METHOD AND SYSTEM FOR EXTRACTING LOWER LIMB VASCULATURE

CROSS-REFERENCE TO RELATED APPLICATIONS

This application is a continuation and claims priority of International Application No. PCT/CN2016/110071 field on Dec. 15, 2016, which claims priority to the following application: Chinese Patent Application No. 201610617709.5 filed on Jul. 30, 2016, the entire contents of which are incorporated herein by reference

TECHNICAL FIELD

The present disclosure generally relates to systems and methods for extracting a vessel, and in particular, to systems and methods for extracting a vessel based on the skeleton segmentation and the vessel segmentation of an angiographic image.

BACKGROUND

Angiography plays an important role in the medical field. Angiography is one of the important methods to diagnose vascular disease. It can diagnose a variety of diseases such as aneurysm, vascular stenosis, and vascular calcification. The angiography techniques include, for example, Digital Subtraction Angiography (DSA), Magnetic Resonance Angiography (MRA), Computed Tomography Angiography (CTA), or the like, or any combination thereof. The segmentation of vessels from other tissues is an important step in angiography. Vessel extraction (or "segmentation", "recognition", "confirmation") based on angiographic images may provide the basis for the diagnosis, treatment, evaluation, virtual surgery and surgical guidance of the disease, and/or help to calculation of vessel diameter, quantitative analysis of vessel images, etc. Since the pixel values or voxel values of vessels and other tissues such as bones in the angiographic images have situations such as approximation, overlapping to a certain extent, in the processing of vessel extraction, bones, and other tissues are easily extracted as vessels, resulting in excessive extraction; or small vessels are removed as non-vascular tissues, resulting in incomplete extraction, and so on. In order to improve the precision of vessel extraction, a variety of methods can be used to segment a vessel.

SUMMARY

According to an aspect of the present disclosure, a method for extracting a vessel of a lower limb is provided. The method may include obtaining an original image including a plurality of image data, in some embodiments, each of the plurality of image data may correspond to a pixel (or a voxel), the plurality of image data may include a target data set, the target data set may represent a first structure; extracting a first reference data set from the plurality of image data, in some embodiments, the first reference data set may include the target data set and a second reference data set, the second reference data set may include data of a second structure; extracting the second reference data set from the plurality of image data; and obtaining the target data set based on the first reference data set and the second reference data set.

According to another aspect of the present disclosure, a non-transitory computer-readable medium is provided. The non-transitory computer readable medium may include executable instructions. When at least one processor executes the instructions, the at least one processor may be caused to effectuate the method for extracting a vessel of the lower limb. The method may include obtaining an original image including a plurality of image data, in some embodiments, each of the plurality of image data may correspond to a pixel (or a voxel), the plurality of image data may include a target data set, the target data set may represent a first structure; extracting a first reference data set from the plurality of image data, in some embodiments, the first reference data set may include the target data set and a second reference data set, the second reference data set may include data of a second structure; extracting the second reference data set from the plurality of image data; and obtaining the target data set based on the first reference data set and the second reference data set.

According to another aspect of the present disclosure, a system related to extracting a vessel of the lower limb is provided. The system may include at least one processor and the executable instructions. When executing the executable instructions, the at least one processor may be configured to cause the system to perform a method for extracting a vessel of a lower limb is provided. The method may include obtaining an original image including a plurality of image data, in some embodiments, each of the plurality of image data may correspond to a pixel (or a voxel), the plurality of image data may include a target data set, the target data set may represent a first structure; extracting a first reference data set from the plurality of image data, in some embodiments, the first reference data set may include the target data set and a second reference data set, the second reference data set may include data of a second structure; extracting the second reference data set from the plurality of image data; and obtaining the target data set based on the first reference data set and the second reference data set.

In some embodiments, the obtaining the target data set may include obtaining a frame data set based on the first reference data set and the second reference data set, in some embodiments, the frame data set may be a subset of the target data set; and performing at least one data supplement operation on the frame data set to obtain the target data set In some embodiments, the first structure may include a vessel, the second structure may include a skeleton, the target data set may include vessel data, the first reference data set may include vessel data and skeleton data, the second reference data set may include skeleton data, and the frame data set may include data of broken vessel segments.

In some embodiments, the extracting the first reference data set may include determining at least one connected domain CD1 in the original image; determining a first seed point based on the at least one connected domain CD1; and performing a regional growth on the original image based on the first seed point and a first threshold to obtain a first image, in some embodiments, pixels or voxels in the first image and data in the first reference data set are bijective.

In some embodiments, the determining the first seed point may include determining values of a boundary distance field of the at least one connected domain CD1 to obtain a data set pfield-1; determining a circularity degree of the at least one connected domain CD1 based on the data set pfield-1; determining a target connected domain based on the at least one connected domain CD1; and determining the first seed point based on the target connected domain.

In some embodiments, the determining the circularity degree of the at least one connected domain CD1 may include determining a radius of the at least one connected domain CD1 based on the data set pfield-1; determining a circular area of the at least one connected domain CD1 based on the radius of the at least one connected domain CD1; and determining the circularity degree of the at least one connected domain CD1 based on the circular area of the at least one connected domain CD1 and an actual area of the at least one connected domain CD1.

In some embodiments, the extracting the second reference data set may include calculating a boundary distance field based on the first image to obtain a data set pfield-2; segmenting the first structure based on the data set pfield-2 to obtain a vessel mask; subtracting the vessel mask from the first image to obtain a first subtraction image; segmenting the second structure based on the first subtraction image to obtain a first skeleton mask; and obtaining a second skeleton mask based on the original image and the first skeleton mask, wherein pixels or voxels in the second skeleton mask and data in the second reference data set are bijective.

In some embodiments, the obtaining the vessel may include performing a regional growth on the first image based on the first seed point to obtain a first vessel mask; and dilating the first vessel mask to obtain the vessel mask.

In some embodiments, the obtaining the first skeleton mask may include calculating a boundary distance field based on the first subtraction image to obtain a data set pfield-3; determining a skeleton seed point based on the data set pfield-3; and performing a regional growth on the first subtraction image based on the skeleton seed point to obtain the first skeleton mask.

In some embodiments, the obtaining the second skeleton mask may include determining a first skeleton region based on the first skeleton mask; and dilating the first skeleton region to obtain a first temporary skeleton mask.

In some embodiments, the obtaining the second skeleton mask may include performing a regional growth on the original image based on a second threshold to obtain a second image; filling the second image to obtain a filled second image; obtaining a superimposition image based on the first temporary skeleton mask and the filled second image; and performing a closing operation on at least one connected domain CD2 in the superimposition image to obtain the second skeleton mask.

In some embodiments, the determining the first skeleton region may include eroding the first skeleton mask to obtain at least one connected domain CD3; and determining the first skeleton region based on the at least one connected domain CD3.

In some embodiments, the determining the first skeleton region may further include designating a connected domain with the maximum area or the maximum volume in the at least one connected domain CD3 as the first skeleton area.

In some embodiments, the obtaining the frame data set may include subtracting the second skeleton mask from the first image to obtain a second subtraction image, wherein pixels or voxels in the second subtraction image and data in the frame data set are bijective.

In some embodiments, the performing at least one data supplement operation on the frame data set may include selecting a second seed point from the frame data set; and performing a regional growth based on a second threshold and the second seed point to obtain the target data set.

In some embodiments, the performing at least one data supplement operation on the frame data set may include extracting a center line of a vessel based on the second subtraction image; and generating the vessel based on the center line of the vessel.

In some embodiments, the extracting the center line of the vessel may include calculating a boundary distance field based on the second subtraction image; obtaining a first vessel growing point and a second vessel growing point based on the boundary distance field; and extracting the center line of the vessel using the shortest route algorithm based on the first vessel growing point and the second vessel growing point.

In some embodiments, the extracting the center line of the vessel may further include determining a second skeleton region in the second skeleton mask; and extracting the center line of the vessel by excluding the second skeleton region.

In some embodiments, the performing at least one data supplement operation on the frame data set may further include ranking data corresponding to the pixels or the voxels in the second subtraction image.

In some embodiments, the performing at least one data supplement operation on the frame data set may further include positioning a region of the second structure based on image data of the original image; segmenting the second structure based on the region of the second structure to obtain a data set for growth control; and expanding the data set for growth control to obtain an expanded data set for growth control, in some embodiments, the expanded data set for growth control may limit the growing of the vessel.

In some embodiments, the positioning the region of the second structure may include obtaining reference image data; extracting a feature of the reference image data; generating a template histogram based on the feature of the reference image data; extracting a feature of the image data based on the feature of the reference image data; generating a sample histogram based on the feature of the image data; and positioning the region of the second structure based on a similarity between the template histogram and the sample histogram.

In some embodiments, the reference image data includes image data of a structure similar to the second structure.

In some embodiments, the feature of the reference image data includes a number or a sectional area of data of the second structure.

In some embodiments, the feature of the image data includes a number or a sectional area of data of the second structure.

In some embodiments, the reference image data and the image data are data from different detection objects.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4-B is a flowchart illustrating an exemplary process for image data processing according to some embodiments of the present disclosure;

FIG. 5-B is a flowchart illustrating an exemplary process for segmenting a vessel according to some embodiments of the present disclosure;

FIG. 6-B is a flowchart illustrating an exemplary process for segmenting a vessel according to some embodiments of the present disclosure;

FIG. 7-B is a flowchart of an exemplary process for extracting a skeleton according to some embodiments of the present disclosure;

FIG. 7-C is a flowchart illustrating an exemplary process for obtaining a first image according to some embodiments of the present disclosure;

FIG. 7-D is a flowchart illustrating an exemplary process for determining a seed point according to some embodiments of the present disclosure;

FIG. 7-E is a flowchart illustrating an exemplary process for obtaining a vessel mask according to some embodiments of the present disclosure;

FIG. 7-F is a flowchart illustrating an exemplary process for obtaining a first skeleton mask according to some embodiments of the present disclosure;

FIG. 7-G is a flowchart illustrating an exemplary process for obtaining a second skeleton mask according to some embodiments of the present disclosure;

FIG. 7-H is a schematic diagram illustrating an exemplary filling operation on a skeleton region according to some embodiments of the present disclosure;

FIG. 10-B is a flowchart illustrating an exemplary process for supplementing foot vessel data according to some embodiments of the present disclosure;

FIG. 10-C is a flowchart illustrating an exemplary process for performing a supplement operation on a data supplement region according to some embodiments of the present disclosure;

FIG. 10-D is a flowchart illustrating an exemplary process for supplementing ilium vessel data according to some embodiments of the present disclosure;

FIG. 10-E is a flowchart illustrating an exemplary process for generating a vessel according to some embodiments of the present disclosure;

DETAILED DESCRIPTION

Figure 1:
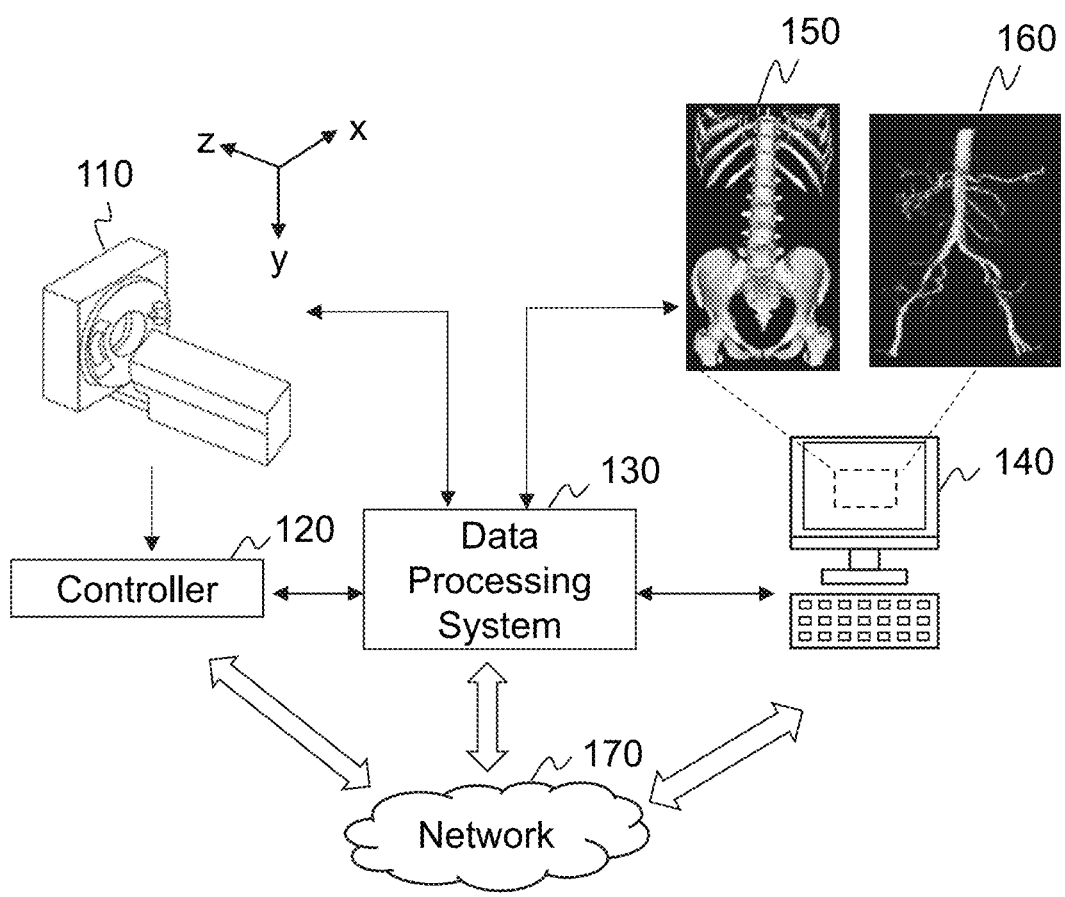
FIG. 1 illustrates a schematic diagram of an exemplary imaging system according to some embodiments of the present disclosure.

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

According to some embodiments of the present disclosure, flowcharts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

During the processing of image data, the terms "image segmentation," "image extraction," and "image classification" may be used interchangeably and may all represent selecting an image that satisfies a condition from a large area. In some embodiments, an imaging system may include one or more configurations. The configurations may include digital subtraction angiograph (DSA), magnetic resonance angiography (MRA), computed tomography (CT), computed tomography angiograph (CTA), ultrasonic scanning (US), positron emission tomography (PET), single-photon emission computerized tomography (SPECT), SPECT-MR, CT-PET, CE-SPECT, DSA-MR, PET-MR, PET-US, SPECT-US, US-CT, US-MR, X-ray-CT, X-ray-US, or the like, or a combination thereof. In some embodiments, a scanning target for imaging may be an organ, an organism, an object, an injured part, a tumor, or the like, or a combination thereof. In some embodiments, the scanning target for imaging may be a head, a thoracic cavity, an abdomen, an organ, a skeleton, a vessel, or the like, or a combination thereof. In some embodiments, the scanning target may be vascular tissues of one or more body parts. In some embodiments, the image may be a two-dimensional image and/or a three-dimensional image. In the two-dimensional image, the delicate distinguishable element may be a pixel. In the three-dimensional image, the delicate distinguishable element may be a voxel. In the three-dimensional image, the image may include a series of two-dimensional slice images and/or two-dimensional image layers.

The image segmentation process may be performed based on a feature of a pixel or a voxel in an image. In some embodiments, the feature of a pixel or a voxel may include texture structure, gray degree, average gray degree, strength, color saturation level, contrast, brightness, or the like, or a combination thereof. In some embodiments, a spatial location feature of a pixel or a voxel may also be used in the image segmentation process.

FIG. 1 illustrates a schematic diagram of an exemplary imaging system according to some embodiments of the present disclosure. An imaging system may include an imaging device 110, a controller 120, a data processing system 130, an input/out device 140, and a network 170.

The imaging device 110 may scan a target object and generate related data and image. The imaging device 110 may also further process the image based on the generated data. In some embodiments, the imaging device 110 may be a single device or a group of devices. In some embodiments, the imaging device 110 may be a medical imaging device, for example, a PET device, a SPECT device, a CT device, a MRI device, or the like. In some embodiments, the device may be used separately or in combination (e.g., a PET-CT device, a PET-MRI device or a SPECT-MRI device). In some embodiments, the imaging device 110 may include a scanner for scanning the target object and obtaining related information (e.g., data). Further, the imaging device 110 may be a radioactive scanning device. The radioactive scanning device may include a radioactive source that may emit radioactive rays to the target object. The radioactive rays may include a particulate ray, a photon ray, or the like, or a combination thereof. The particulate ray may include neutron, proton, α ray, electron, μ medium, heavy ion, or the like, or a combination thereof. The photon ray may include X-ray, γ ray, ultraviolet ray, laser, or the like, or a combination thereof. In some embodiments, the photon ray may be an X-ray and the corresponding imaging device 100 may be a CT system, a digital radiography (DR) system, a multimodal medical imaging system, or the like, or a combination thereof. In some embodiments, the multimodal medical imaging system may include a CT-PET system, a SPECT-MRI system, or the like, or a combination thereof. In some embodiments, the imaging device 110 may include a ray generation unit and a ray detection unit (not shown). For example, the imaging device 110 may include a photon detector for generating rays, and/or detecting rays, etc. For example, the photon detector may generate a photon used for scanning the target object or detect a photon that has scanned the target object. In some embodiments, the imaging device 110 may be a CT imaging system or a multimodal medical imaging system based on CT whose photon detector may include an X-ray detector.

Image data generated by the imaging device 110 may be processed according to a coordinate system rule. In some embodiments, the image data may be processed according to the Descartes rectangular coordinate system. In the Descartes rectangular coordinate system, the x-direction may refer to a direction of a frontal axis (a direction of an intersecting line of a coronal section and a horizontal plane). For example, the direction of a frontal axis may refer to a direction from an imaged object's right side to the imaged object's left side or a direction from an imaged object's left side to the imaged object's right side. The y-direction may refer to a direction of an anteroposterior axis (a direction of an intersecting line of a vertical plane and a horizontal plane). For example, the direction of an anteroposterior axis may refer to a direction from an imaged object's back part to the imaged object's front part or a direction from an imaged object's front part to the imaged object's back part. The z-direction may refer to a direction of a vertical axis (a direction of an intersecting line of a coronal section and a vertical plane). For example, the direction of the vertical axis may refer to a direction from an imaged object's top to the imaged object's bottom or a direction from an imaged object's bottom to the imaged object's top. It should be noted that the X coordinate, the Y coordinate, and the Z coordinate shown in FIG. 1 are provided for illustration purposes, and not to intended to limit the scope of the X coordinate, the Y coordinate, and the Z coordinate.

The controller 120 may control the imaging device 110, the input/output device 140, and/or the data processing system 130. In some embodiments, the controller 120 may control the X-ray generation unit and/or the X-ray detection unit in the imaging device 110. The controller 120 may receive information from the imaging device 110, the input/output device 140 and/or the data processing system 130 or transmit information to the system(s)/device(s) above. In some embodiments, the controller 120 may receive data related to the target object or an image signal from the imaging device 110. The controller 120 may transmit the data related to the target object or the image signal to the data processing system 130. The controller 120 may receive processed data or reconstructed image from the data processing system 130. The controller 120 may transmit the processed data or the reconstructed image to the input/output device 140. In some embodiments, the controller 120 may include a computer, a program, an algorithm, software, a storage device, interfaces, or the like. The interfaces may include interfaces among the imaging device 110, the input/output device 140, the data processing system 130 and/or other modules or units in the imaging system.

In some embodiments, the controller 120 may receive instructions from a user (e.g., a doctor, an imaging technician). The controller 120 may receive the instructions from the user via the input/output device 140. The controller 120 may receive the instructions or convert the instructions to control the imaging device 110, the input/output device 140, and/or the data processing system 130. For example, the controller 120 may process data input by a user via the input/output device 140 and transform the data into one or more corresponding instructions. The instructions may include a scanning time, positioning information of a scanned target, a rotating velocity of a frame, a scanning parameter, or the like, or a combination thereof. The controller 120 may control the data processing system 130 to select different algorithms to process the image data.

The data processing system 130 may process information received from the imaging device 110, the controller 120, the network 170, and/or the input/output device 140. In some embodiments, the data processing system 130 may generate one or more CT images based on the information. The data processing system 130 may transmit the images to the input/output device 140. The data processing system 130 may perform various operations related to data processing. The various operations may include data preprocessing, data transformation, data cleaning, data fitting, data weighting processing, or the like, or a combination thereof. The data processing system 130 may implement the data processing based on different algorithm routines. The algorithm routines may include Fourier transformation principle, filtering back projection principle, iteration reconstruction, histogram swelling calculation, image data function optimization, level set function calculation, or the like, or a combination thereof. In some embodiments, the data processing system 130 may process data related to an image of a vessel.

For example, the data processing system 130 may recognize skeleton in the chest and the abdomen 150, a vessel of the abdominal 160, a vessel of a lower limb, a center line of a vessel, or vessels in other parts. In some embodiments, the data processing system 130 may position a vessel or a skeleton in an image using multiple algorithm routines or methods, for example, the data processing system 130 may position a rib, an ilium, a sacrum, a tibia, an iliac artery, or the like.

In some embodiments, the data processing system 130 may generate a control signal related to the imaging device 110. In some embodiments, processed (and/or unprocessed) data result processed by the data processing system 130 may be transmitted to other modules or units in the system. The other modules or units may refer to a database (not shown), a terminal receiver of the network 170 (not shown). The data processing system 130 may be capable of storing the unprocessed data and/or processed data. In some embodiments, the data information corresponding to the data processing system 130 may be further processed, transmitted to storage to be stored, and/or transmitted to a terminal.

The input/output device 140 may receive, transmit or display information. In some embodiments, the input/output device 140 may include a keyboard, a touch-sensitive device, a mouse, an audio input device, an image input device, a remote control device, or the like, or a combination thereof. The input/output device 140 may include a program, software, an algorithm, data, a signal, a text, a number, an image, audio, or the like, or a combination thereof. In some embodiments, a user may input a plurality of initial parameters or set an initialization condition for corresponding image processing. In some embodiments, the input information may be from an external data source (e.g., a soft disk, a rigid disk, a light disk, a storage chip, a wired terminal, a wireless terminal, or a combination thereof). The input/output device 140 may receive information from other modules or units in the system and/or transmit information to other modules or units in the system. In some embodiments, the input/output device 140 may transmit information to a terminal (e.g., a display screen, a printer, a storage device, a computing device, or a combination thereof) to perform corresponding operations. Specifically, in some embodiments, the input/output device 140 may include a graphical user interface used to display information on steps of the imaging process or an image processing result (e.g., an image histogram, a skeleton mask, a vessel mask, the images related to a vessel by image transformation, or a combination thereof). The graphical user interface may provide a notification for a user to input a parameter, and/or direct the user to participate the data processing process (e.g., start or stop the processing, select or amend operating parameters, select or amend an algorithm, amend a program, exit the system, upgrade the system, update the system).

The network 170 may be a single network or a combination of a plurality of different networks. For example, the network 170 may include a local area network (LAN), a wide area network (WAN), a public network, a private network, an exclusive network, a public switched telephone network (PSTN), the Internet, a wireless network, a virtual network, or the like, or a combination thereof. The network 170 may also include a plurality of network access points. The wired network may be a network that is implemented via, for example, a metal cable, a composite cable, one or more access points, or the like, or a combination thereof. The wireless network may be a network that is implemented via, for example, Bluetooth, LAN, WAN, ZigBee, near field communication (NFC), or the like, or a combination thereof. The network 170 may be suitable in the scope of the present disclosure but is not limited the description.

In some embodiments, the imaging device 110, the controller 120, the data processing system 130, and the input/output device 140 may be connected with each other directly or indirectly. In some embodiments, the imaging device 110, the controller 120, the data processing system 130, and the input/output device 140 may be connected with each other directly via the network 170. In some embodiments, the imaging device 110, the controller 120, the data processing system 130, and the input/output device 140 may be connected with each other indirectly by one or more intermediary units (not shown). The intermediary units may be tangible or intangible (e.g., wireless electric wave, optical wave, acoustic wave, electromagnetic wave, or the like, or a combination thereof). Different modules and units may be connected to each other by a wireless connection and/or a wired connection.

The CT system is merely an embodiment of the imaging device 110, and the present disclosure is not limited in the scope of the embodiment. The CT system may be used in various application scenarios such as medicine, industry, etc. Furthermore, the scanning results of the CT system may be used in various analyses, for example, diagnose analysis, safety scan, defect detection, quantitative analysis, failure analysis, or the like, or a combination thereof.

It should be noted that the above description of the image processing system is provided for the purpose of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications may not depart from the spirit and scope of this disclosure.

Figure 2:
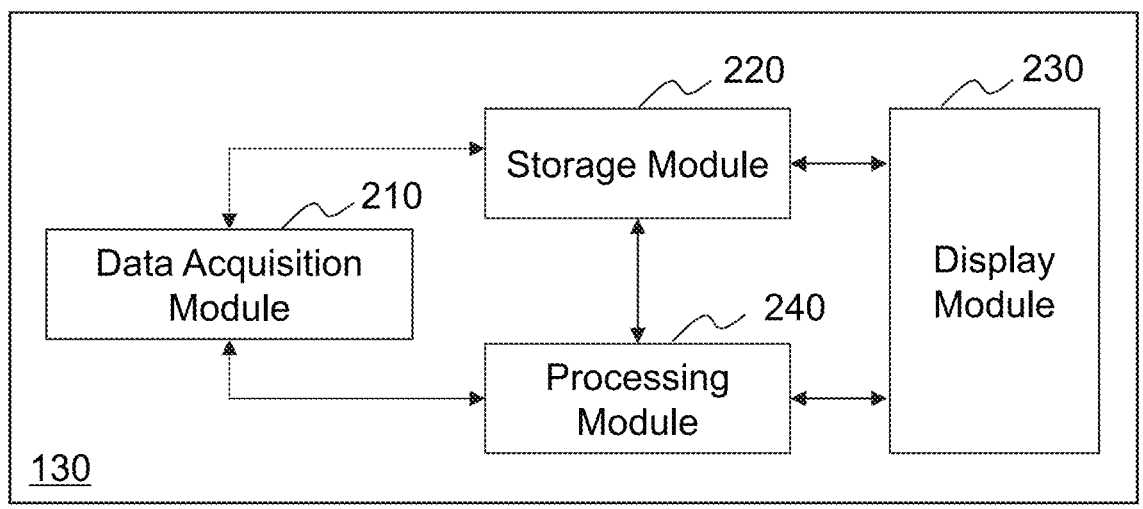
FIG. 2 is a schematic diagram of the data processing system according to some embodiments of the present disclosure.

FIG. 2 is a schematic diagram of the data processing system 130 according to some embodiments of the present disclosure. The data processing system 130 may include one or more data acquisition modules 210, storage modules 220, one or more display modules 230, and one or more processing modules 240. The modules may be connected with each other directly (and/or indirectly).

The data acquisition module 210 may obtain data. The obtained data may be from the imaging device 110 and/or the controller 120. In some embodiments, the data may be obtained via the network 170 from an external source. The data may be three-dimensional data and/or two-dimensional data. The data may be data that is obtained from a specific part according to detection requirements. The data may include a panoramic scan of a target object, a chest, a lung, a lower limb, a bronchus, a skeleton, a vessel, a nerve distribution of a target object, or the like, or a combination thereof. In some embodiments, the data may be angiographic data. In some embodiments, the data acquisition module 210 may obtain original data of an image of a vessel, data of a processed image of the vessel, or a processing parameter of the image of the vessel, etc.

The storage module 220 may store data or information. The stored data or information may be from the imaging device 110, and/or the controller 120, and/or other modules/units of the data processing system 130 (e.g., the data acquisition module 210, the display module 230, the processing module 240, other modules (not shown). The stored data or information may be in various forms, for example, numerical value, signal, image, related information of a target object, command, algorithm, program, or the like, or a combination thereof. In some embodiments, the stored data or information may be an image of a vessel, a parameter of the image of the vessel, data of the image of the vessel, data of processed image of the vessel, a program and/or an algorithm used to process the image of the vessel, etc.

The storage module 220 may include a rigid disk, a soft disk, a random access memory (RAM), a dynamic random access memory (DRAM), a static random access memory (SRAM), a bubble memory, a thin film memory, a magnetic plated wire memory, a phase change memory, a flash memory, a cloud disk, or the like, or a combination thereof. The storage module 220 may provide a temporary storage, that is, the storage module 220 may load and store data for a next data processing. The storage module 220 may provide a permanent storage, that is, the storage module 220 may store final data processing results. The storage module 220 may be an immobile storage system (e.g., a disk) and/or a mobile storage system (e.g., a USB port, a port (e.g., a hot wire port), a drive (e.g., a disk drive). The storage module 220 may be connected to one or more data acquisition modules 210, display modules 230, processing modules 240, or other modules (not shown). In some embodiments, the storage module 220 may be selectively connected to one or more virtual storage resources (e.g., a cloud storage, a virtual private network, and/or other virtual storage resources) via the network 170.

The display module 230 may display data. The displayed data information may be from the data acquisition module 210, the storage module 220, and/or the processing module 240. The displayed data may be transmitted to the input/output device 140. In some embodiments, the display module 230 may transmit the image data obtained by the processing module 240 to a terminal to display. In some embodiments, the display module 230 may directly display related data information from the network 170 or the storage module 220. The data may be displayed in various forms including an acoustic form (e.g., voice) and/or a vision form (e.g., text, video, graph), or the like, or a combination thereof. The displayed data may be in various forms including a numerical value, a signal, an image, related information of a target object, a command, an algorithm, a program, or the like, or a combination thereof. In some embodiments, the display module 230 may display an image including vessel information (e.g., a histogram, a gray scale image of a vessel, an image of a vessel mask, an image of rough segmentation of a vessel, an image of precise segmentation of a vessel, an image of skeleton segmentation)

The processing module 240 may process related data and construct an image based on the related data. The data may be from the data acquisition module 210, the storage module 220, other modules not shown and/or an external resource obtained via the network 170. The constructed image may be transmitted to the display module 230, etc. The data processed by the processing module 240 may be data related to a specific part of a target object. The specific part may include a heart, a vessel, a liver, a spleen, a kidney, a skeleton, or the like, or a combination thereof. For example, the processing module 240 may process data of a vessel of an abdomen vessel and a vessel of a lower limb. The processing module 240 may process the data based on a plurality of methods. In some embodiments, a user may select the data that needs to be processed. For example, the user may select a vessel of a designated part in an image to be processed. In some embodiments, the data may be processed based on one or more algorithms, for example, histogram fitting, image transformation processing, data weighting processing, or the like.

The processing module 240 may include a general processor. The general processor may include but is not limited a programmed logic device (PLD), an application special integrated circuit (ASIC), a microprocessor, a system on chip (SOC), a digital signal processor (DSP), or the like, or a combination thereof. In some embodiments, two or more processors may be integrated into a hardware device. In some embodiments, the two or more processors may be independent of or connected with each other. The processors may process data by a plurality of methods including by hardware, by software, by a combination of hardware and software, or the like.

It should be noted that the above description of the data processing system 130 is provided for the purpose of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications may not depart from the spirit and scope of this disclosure.

Figure 3:
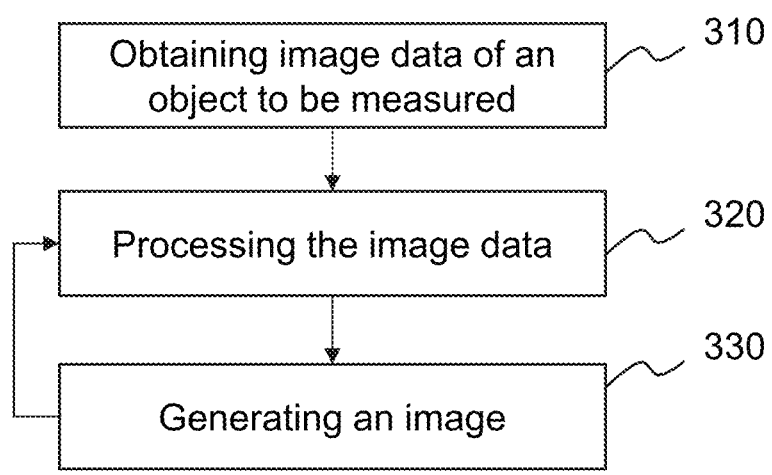
FIG. 3 is a flowchart illustrating an exemplary process for image generation according to some embodiments of the present disclosure.

FIG. 3 is a flowchart illustrating an exemplary process for image generation according to some embodiments of the present disclosure. In some embodiments, the data processing system 130 may perform the image generation process. The image generation process may include obtaining image data of a measured object 310, processing the image data 320, and generating an image 330.

In 310, image data of a measured object may be obtained. The measured object may include a human body, an animal, or a part of the human body or the animal. For example, the part may include an organ, tissue, a diseased part, a tumor part, or the like, or a combination thereof. For example, the measured object may include but is not limited a head, a chest, an abdomen, a heart, a liver, a spleen, a kidney, an upper limb, a lower limb, a backbone, a skeleton, a vessel, or the like, or a combination thereof. The image data of the measured object may be two-dimensional image data or three-dimensional image data. The image data of the measured object may be MRA image data, CTA image data, PET image data, or the like, or a combination thereof. In some embodiments, the data acquisition module 210 may implement 310. In some embodiments, the image data of the measured object may be obtained from the storage module 220. In some embodiments, the image data of the measured object may be obtained from an external data source via the network 170. In some embodiments, the image data of the measured object may be obtained from the input/output device 140.

In 320, the obtained image data of the measured object may be processed. The image data processing may include one or more sub-steps. In some embodiments, the processing module 240 may implement 320. In some embodiments, the image data processing may include deletion of unreliable data or correction of a value of data. In some embodiments, the image data processing may include filtration of data noise, etc. In some embodiments, the image data processing may include image segmentation, image rendering, image transformation, or the like. In some embodiments, the image data processing may be based on one or more algorithms, for example, swelling, corrosion, the regional growth method, the level set algorithm, the gradient descent method, the single source shortest route algorithm, or the like, or a combination thereof.

In 330, an image may be generated based on the processed image data in 320. The display module 230 or the processing module 240 may implement 330. The image generation operation may be based on one or more algorithms, for example, the image transformation algorithm, the image displaying algorithm, or the like, or a combination thereof. The image transformation algorithm may include a transformation from frequency domain to image domain, a transformation of a gray image, or the like. The image displaying algorithm may include an algorithm of adjusting the image's parameters including color, contrast ratio, brightness, or the like.

It should be noted that the above descriptions about the processing of the image generation are provided for illustration purposes, and should not be designated as the only practical embodiment. For persons having ordinary skills in the art, after understanding the general principle of the process for the image generation, without departing the principle, may modify or change the forms or details of the particular practical ways and steps, and further make simple deductions or substitutions, or may make modifications or combinations of some steps without further creative efforts. However, those variations and modifications do not depart the scope of the present disclosure. In some embodiments, steps 320 and 330 may be combined into an independent operation. In some embodiments, before step 330, the image processing process may return to 320 to further process the image data. In some embodiments, steps 330 and 320 may be performed simultaneously. In some embodiments, one or more operations may be added to the flowchart or be omitted from the flowchart. For example, a scanning operation of the measured object may be added before step 310. The measured object may be scanned by the imaging device 110. As another example, a data storage operation may be added among, before, or after step 310, 320, and/or 330. The data may be stored in the storage module 220.

Figure 4A:
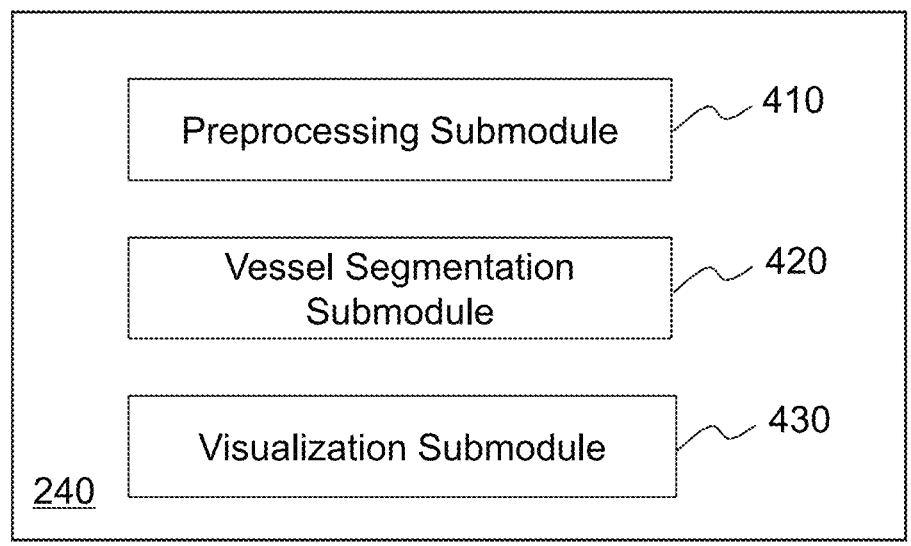
FIG. 4-A is a schematic diagram illustrating an exemplary processing module according to some embodiments of the present disclosure.
Figure 4B:
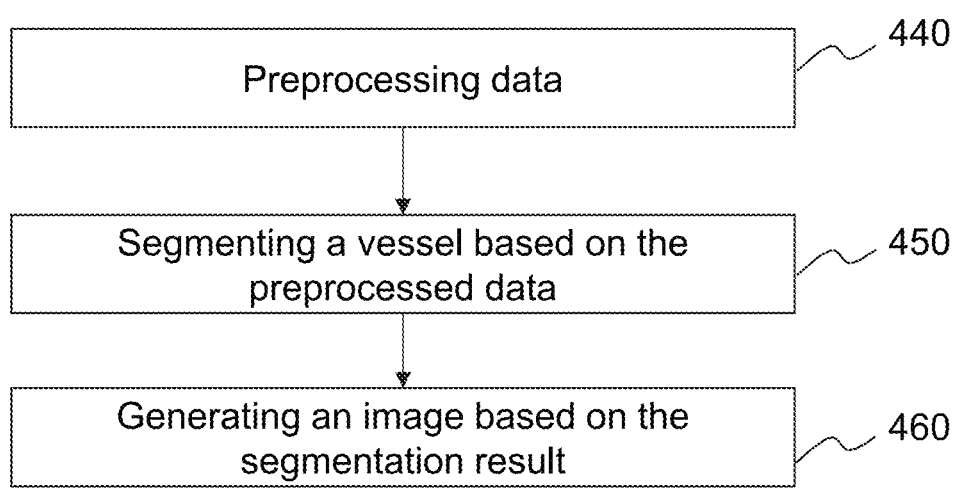

FIG. 4-A is a schematic diagram illustrating an exemplary processing module 240 according to some embodiments of the present disclosure. The processing module 240 may include a preprocessing submodule 410, a vessel segmentation submodule 420, and a visualization submodule 430.

The preprocessing submodule 410 may preprocess image data. The image data preprocessing may make the data suitable for vessel segmentation. The image data preprocessing may include image normalization, image reconstruction, image smoothing, image compression, image enhancement, image matching, image registration, image geometric correction, elimination of image mutation or noise, or the like, or any combination thereof. In some embodiments, the preprocessing submodule 410 may be omitted.

The vessel segmentation submodule 420 may segment a vessel from an image including vessels. The segmented vessel may include vessel(s) of one or more body parts of a subject, for example, a vessel of a head and neck, a thoracic vessel, a vessel of an abdomen, a vessel of an upper limb, a vessel of a lower limb, a vessel of a foot, etc. The segmented vessel may include a vessel within an organ of the subject, for example, a vessel of a brain, a vessel of a heart, a vessel of a liver, a vessel of a spleen, a vessel of a kidney, etc. In some embodiments, the vessel segmentation submodule 420 may segment a characteristic line of a vessel. The characteristic line of a vessel may refer to one or more lines, points, or the like, or any combination thereof, such as a center line of a vessel, a boundary line of the vessel, an endpoint of the vessel, etc. The characteristic line of the vessel may be a collection of one or more pixels (or voxels) located within or at the boundary of the vessel. In some embodiments, the characteristic line of the vessel may refer to a line located at or near the center of the vessel and/or a line representing a trend of the vessel. In some embodiments, the center line of the vessel may refer to a line connecting pixels (or voxels) with equal distances to the vessel boundary. In some embodiments, the boundary line of the vessel may refer to a line located at a wall of the vessel or near the wall of the vessel, and may represent a boundary between the vessel and non-vascular parts. The vessel may include a collection of pixels within the center line of the vessel and the boundary line of the vessel. The endpoint of the vessel may refer to one or more pixels (or voxels) at the end of the vessel. In some embodiments, the end of the vessel may be an end of the vessel in anatomy. In some embodiments, the endpoint of the vessel may be an end of the vessel within a range that is manually or automatically determined, for example, an end region of the vessel within a displayable range of an image.

In some embodiments, the vessel segmentation submodule 420 may include a storage unit for storing one or more programs or algorithms, such as a threshold-based segmentation method, an edge-based segmentation method, a region-based segmentation method, a segmentation method based on cluster analysis, a segmentation method based on Wavelet Transform, a segmentation method based on mathematical morphology, a method based on artificial neural network, a method based on genetic algorithm, and a combination method of vessels of the same or different parts.

The visualization submodule 430 may perform a visualization processing on the image data. The visualization submodule 430 may convert the data into a visual form. The visualized image may be a gray scale image or a color image. The visualized image may be a two-dimensional image or a three-dimensional image. The visualized image may be displayed on the input/output device 140 or printed by a printer. In some embodiments, the image data for visualization processing may be obtained from the preprocessing submodule 410 and/or the vessel segmentation submodule 420.

FIG. 4-B is a flowchart illustrating an exemplary process for processing image data according to some embodiments of the present disclosure. The process for processing image data may include preprocessing data 440, segmenting a vessel 450, and generating an image of the vessel 460.

In 440, the data may be preprocessed. The preprocessing submodule 410 may perform 440. The data preprocessing may include image smoothing, image denoising, image enhancement, or the like, or any combination thereof. The image smoothing may be performed in the image domain or the frequency domain. In some embodiments, pixels (or voxels) in the image may be processed directly by the image smoothing in the image domain. In some embodiments, the image smoothing in the frequency domain may include converting the image data in the image domain into the image data in the frequency domain, processing the image data in the frequency domain, and converting the processed image data in the frequency domain into the image data in the image domain. The image smoothing may include median smoothing, Gaussian smoothing, average smoothing, normalized smoothing, bilateral filtering smoothing, or the like, or any combination thereof. Noise in the image may be removed by the image denoising. In some embodiments, the image denoising may be performed according to one or more denoising models, for example, Gaussian filtering, anisotropy diffusion equation model, bilateral filtering, total variation model, Wavelet transform filtering, or non-local means, or the like.

In 450, the vessel may be segmented. The vessel segmentation submodule 420 may perform 450. The vessel segmentation may be based on the preprocessing result in 440. In some embodiments, the vessel segmentation may be based on data obtained directly from the data acquisition module 210, the storage module 220, or the input/output device 140, or data obtained from an external data source via the network 170. The vessel segmentation may be performed according to one or more image segmentation algorithms, for example, a gradient descent method, a threshold method, a regional growth method, a level set method, region segmentation and/or merging, an edge tracking segmentation method, a statistical pattern recognition method, a mean clustering segmentation method, a manual calibration method, a topology refinement method, a distance transformation method, or the like, or any combination thereof. In some embodiments, the vessel segmentation method may be stored in the vessel segmentation submodule 420, the storage module 220, or mobile storage devices (e.g., a portable hard disk, a USB flash disk). In some embodiments, the vessel segmentation method may be obtained from one or more external data sources via the network 170.

In 460, an image of the vessel may be generated. The image of the vessel may be generated based on the result of the segmented vessel obtained in 450. The visualization submodule 430 may perform 460. In some embodiments, a color image may be generated. In some embodiments, a gray scale image may be generated. In some embodiments, step 460 may be performed according to one or more post-processing operations. The post-processing operations may be based on two-dimensional post-processing techniques including, for example, a multi-planar recombination technique, a cured surface reconstruction technique, a volume reconstruction technique, a volume rendering technique, or the like, or any combination thereof. The post-processing operation may be based on three-dimensional post-processing techniques including, for example, a three-dimensional surface reconstruction technique, a three-dimensional volume reconstruction technique, a volume intensity projection technique, a maximum intensity projection technique, a minimum intensity projection technique, an average density projection technique, or the like, or any combination thereof. Other possible techniques may include repair, rendering, filling, or the like, or any combination thereof.

It should be noted that the above descriptions about the processing module and the process for processing image data are provided for illustration purposes, and should not be designated as the only practical embodiment. Each submodule may be implemented by one or more components, and the function of each submodule is not limiting. Each submodule may be added or omitted in specific scenarios. For persons having ordinary skills in the art, after understanding the general principle of the process for processing image data without departing the principle, may modify or change the forms or details of the particular practical ways and steps, and further make simple deductions or substitutions, or may make modifications or combinations of some steps without further creative efforts. However, those variations and modifications do not depart the scope of the present disclosure. For example, the preprocessing submodule 410 and/or the preprocessing data 440 may be omitted. As another example, 440 and 450 may be combined into one operation. As yet another example, 450 and 460 may be performed simultaneously or alternately.

Figure 5A:
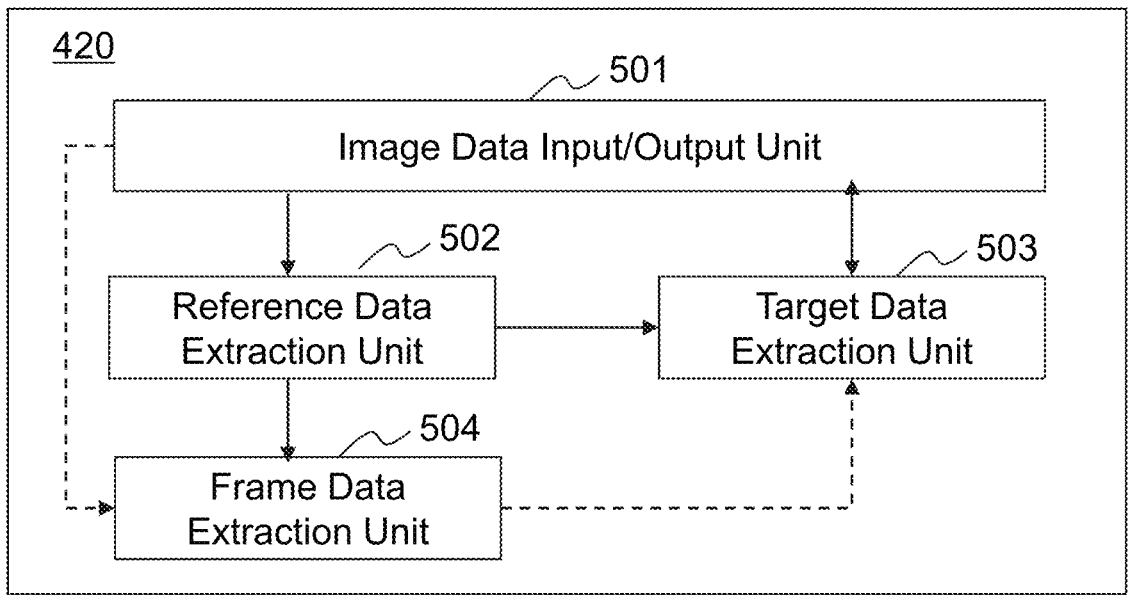
FIG. 5-A is a schematic diagram illustrating an exemplary vessel segmentation submodule according to some embodiments of the present disclosure.
Figure 5B:
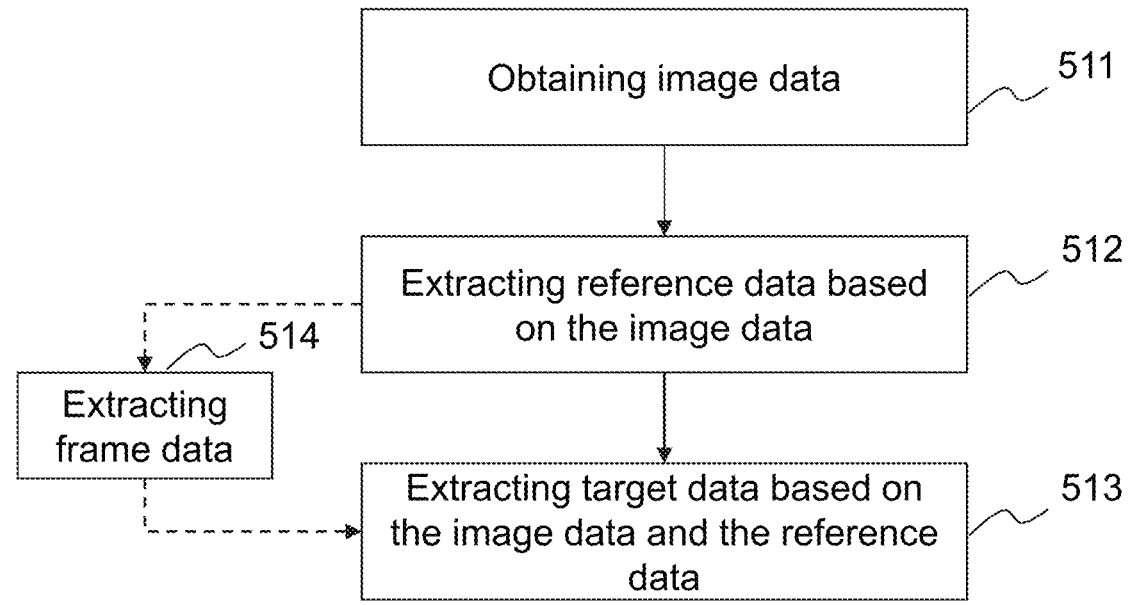

FIG. 5-A is a schematic diagram illustrating an exemplary vessel segmentation submodule 420 according to some embodiments of the present disclosure. The vessel segmentation submodule 420 may include an image data input/output unit 501, a reference data extraction unit 502, a target data extraction unit 503, and/or a frame data extraction unit 504.

The image data input/output unit 501 may input and/or output image data. The image data may refer to values of pixels (or voxels) in the image. The image data may include vessel data and/or non-vessel data (e.g., skeleton data, fat data, data of other types of tissue). In some embodiments, the input image data may be data obtained by the data acquisition module 210, data preprocessed by the preprocessing submodule 410, data input by the input/out device 140, and/or data obtained via the network 170. The data output by the image data input/output unit 501 may be vessel data after the vessel segmentation processing, and data generated in the intermediate process of the vessel segmentation process (e.g., skeleton data, fat data, data of other tissues). In some embodiments, the data output by the image data input/output unit 501 may be data extracted by the reference data extraction unit 502 and/or data extracted by the target data extraction unit 503.

The reference data extraction unit 502 may extract reference data. In some embodiments, the reference data may include one or more sets of skeleton data. The skeleton data may refer to image data corresponding to a skeleton tissue. In some embodiments, the skeleton tissue may include a skeleton of a lower limb, for example, a tibias, an ilia, a sacrum, and/or a foot bone, etc. In some embodiments, the skeleton tissue may include a skeleton tissue of a chest and/or an abdomen, for example, vertebrae, and/or a rib, etc. In some embodiments, the skeleton tissue may include a skeleton tissue of a head and/or a cervix, for example, a skull, and/or neck vertebrae, etc. In some embodiments, the reference data extraction unit 502 may extract one or more sets of skeleton data in the image data. In some embodiments, the reference data extraction unit 502 may extract one or more sets of non-skeleton data (e.g., vessel data, fat data, data of other types of tissues) when extracting skeleton data. For example, the data extracted by the reference data extraction unit 502 may include most of the skeleton data and/or a small amount of vessel data, or data of other tissues in the image data. In some embodiments, the reference data may include a first reference data set. The first reference data set may include a target data set and/or a second reference data set. For example, the first reference data set may include the skeleton data and the vessel data. As another example, the second reference data set may include the skeleton data.

The target data extraction unit 503 may extract target data. In some embodiments, the target data may include one or more data about one or more vessels, that is, vessel data. The vessel data may refer to image data corresponding to the vessel(s). The vessel may be an artery vessel, a vein, etc. In some embodiments, the vessel may include a vessel of a lower limb, for example, an iliac artery (or vein), a femoral artery (or vein), a popliteal artery (or vein), a tibial artery (or vein), a fibular artery (or vein), an ankle artery (or veins), and/or a pedal artery (or vein), etc. In some embodiments, the vessel may include a vessel of an abdomen, for example, an abdominal aorta (or vein), a hepatic artery (or vein), a splenic artery (or vein), and/or a renal artery (or vein), etc. In some embodiments, the vessel may include a thoracic vessel, for example, an intercostal artery (or vein), a pulmonary artery (or vein), aorta (or vein), a bronchial artery (or vein), an esophageal artery (or vein), and/or a gastric artery (or vein), etc. In some embodiments, the vessel may include a vessel of an upper limb, for example, an axillary artery (or vein), a brachial artery (or vein), a radial artery (or vein), and/or an ulnar artery (or vein), etc. In some embodiments, the vessel may include a vessel of a head and neck, for example, a left/right internal carotid artery (or vein), a left/right external carotid artery (or vein), a left/right common carotid artery (or vein), a vertebral artery (or vein), an occipital artery (or vein), a posterior auricular artery (or vein), a superficial temporal artery (or vein), a lingual artery (or vein), an ophthalmic artery (or vein), a cerebral artery (or vein), etc. In some embodiments, the vessel data may include data relating to the vessel, for example, data of a centerline of the vessel, a boundary line of the vessel, or an endpoint of the vessel.

In some embodiments, the extraction of the target data may be performed based on the data (e.g., the vessel data, the skeleton data, the fat data, and/or other data of tissues) input by the image data input/output unit 501, and/or the reference data (e.g., the skeleton data, the fat data, and/or other data of tissues) extracted by the reference data extraction unit 502. In some embodiments, the extraction of the target data may also be performed based on the frame data extracted by the frame data extraction unit 504. In some embodiments, the target data extraction unit 503 may extract one or more other data when extracting the target data. For example, if the target data are vessel data, other data may include the skeleton data, the fat data, or data of other tissues, etc.

The frame data extraction unit 504 may extract a frame data set. The frame data set may include one or more target data. In some embodiments, the frame data set may include one or more target data that are easy to be extracted. For example, if the target data are vessel data, the frame data set may include one or more data of vessels with relatively large diameters in the image data (e.g., an abdominal aorta, a tibial artery, and/or an iliac artery). As another example, if the target data are vessel data, the vessels near the skeleton are difficult to be extracted, and the frame data set may include data of vessels at a specific distance from the skeleton.

FIG. 5-B is a flowchart illustrating an exemplary process for segmenting a vessel according to some embodiments of the present disclosure. The process for segmenting a vessel may include obtaining image data 511, extracting reference data 512, and extracting target data 513.

In 511, image data may be obtained. The image data may be obtained from the data acquisition module 210, the storage module 220, the display module 230, the input/out device 140, and/or the preprocessing submodule 410, or obtained via the network 170. The image data input/output unit 501 may perform 511.

In 512, reference data may be extracted. The reference data may be extracted by using one or more segmentation methods. The segmentation methods may include a threshold method, a regional growth method, a method based on energy function, a level set method, a regional segmentation and/or merging, an edge tracking segmentation method, a statistical pattern recognition method, a mean clustering segmentation method, a model method, a segmentation method based on deformable model, an artificial neuron network method, a minimum path segmentation partition method, a tracking method, a rule-based segmentation method, a coupling surface segmentation method, or the like, or any combination thereof. The reference data extraction unit 502 may perform 512.

In 513, target data may be extracted. The target data may be extracted by using one or more segmentation methods according to the present disclosure. In some embodiments, the extraction of the target data may be performed based on the image data obtained in step 511 and the reference data extracted in 512. For example, the reference data extracted in 512 may be removed from the image data obtained in step 511 to obtain a result of removing the reference data, and the target data may be extracted based on the result of removing the reference data. The target data extraction unit 503 may perform 513.

In some embodiments, 514 may be added before 513. In 514, the frame data set may be extracted. The extraction of the frame data set may be performed based on the image data obtained in 511 and/or the reference data extracted in 512. In some embodiments, the frame data may be extracted by using one or more segmentation methods according to the present disclosure. For example, the reference data may be removed from the image data to obtain the frame data set, and/or one or more image segmentation processes may be performed to obtain the frame data set. The frame data extraction unit 504 may perform 514. In 513, the extraction of the target data may be performed based on the frame data set extracted in 514. For example, a regional growth may be performed based on the frame data to obtain the target data.

It should be noted that the above descriptions about the vessel segmentation submodule and the process for segmenting the vessel are provided for illustration purposes, and should not be designated as the only practical embodiment. Each unit may be implemented by one or more components, and the function of each unit is not limiting. Each unit may be added or omitted in specific scenarios. For persons having ordinary skills in the art, after understanding the general principle of the process for segmenting the vessel, without departing the principle, may modify or change the forms or details of the particular practical ways and steps, and further make simple deductions or substitutions, or may make modifications or combinations of some steps without further creative efforts. For example, the image data input/output unit 501, the frame data extraction unit 504, the obtaining image data 511, and/or the extracting frame data 514 may be omitted. As another example, a data storage operation may be added between 511, 512, 513, and/or 514, and the data may be stored in the storage module 220. As yet another example, one or more other image processing operations may be added to 511, 512, 513, and/or 514, such as image dilation, image erosion, etc.

Figure 6A:
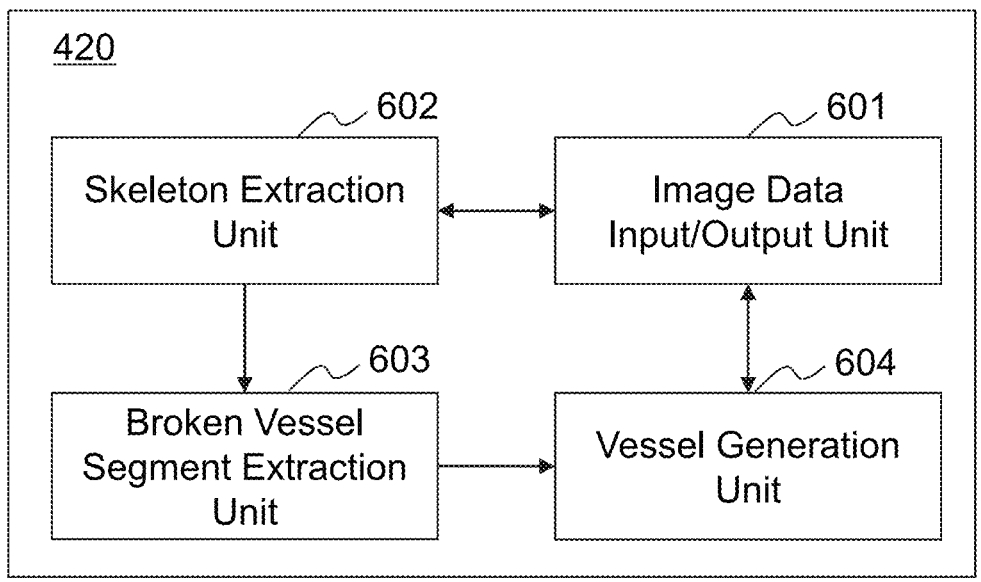
FIG. 6-A is a schematic diagram illustrating an exemplary vessel segmentation submodule according to some embodiments of the present disclosure.
Figure 6B:
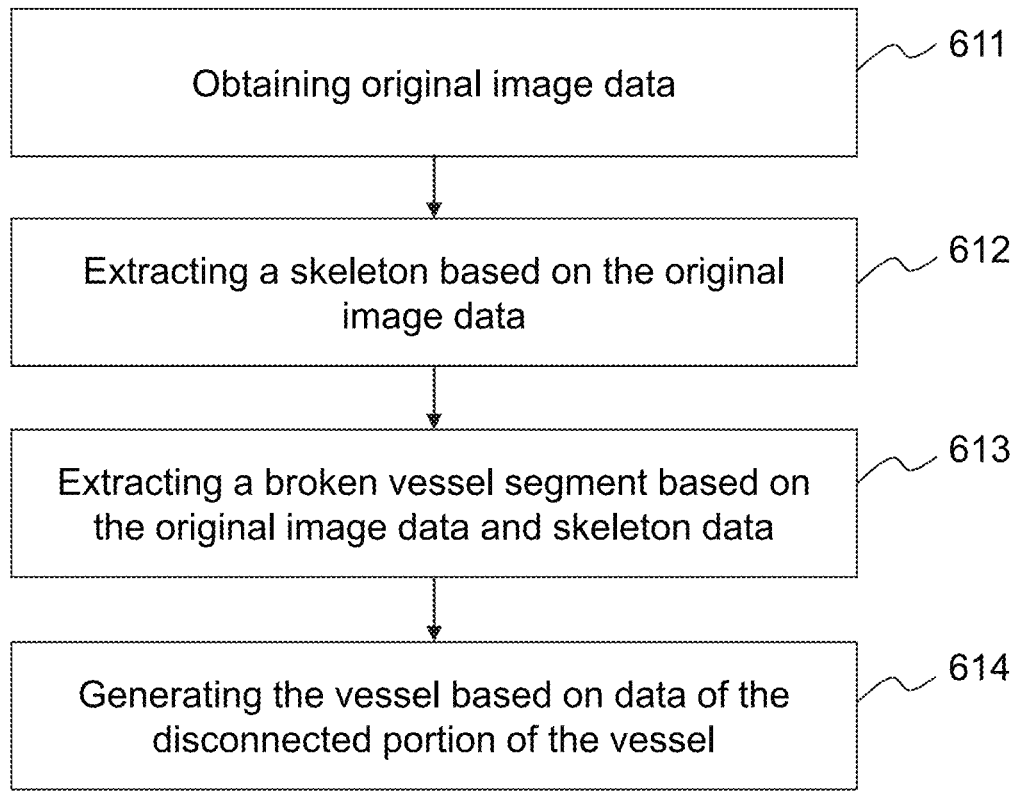
Figure 7A:
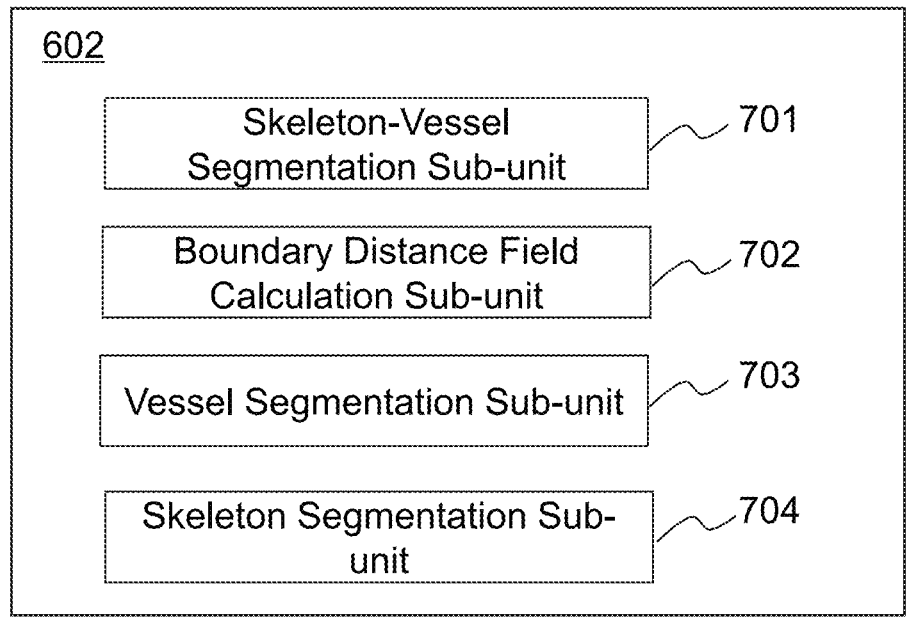
FIG. 7-A is a schematic diagram illustrating an exemplary skeleton extraction unit according to some embodiments of the present disclosure.
Figure 7B:
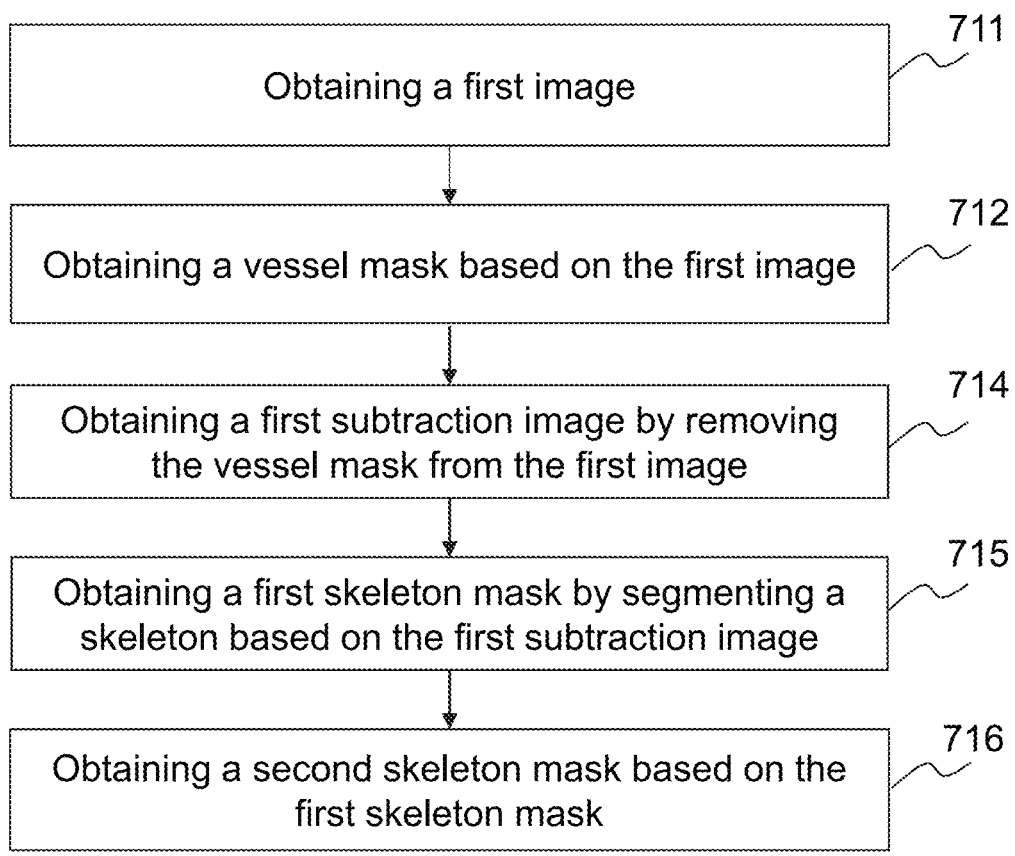
Figure 7C:
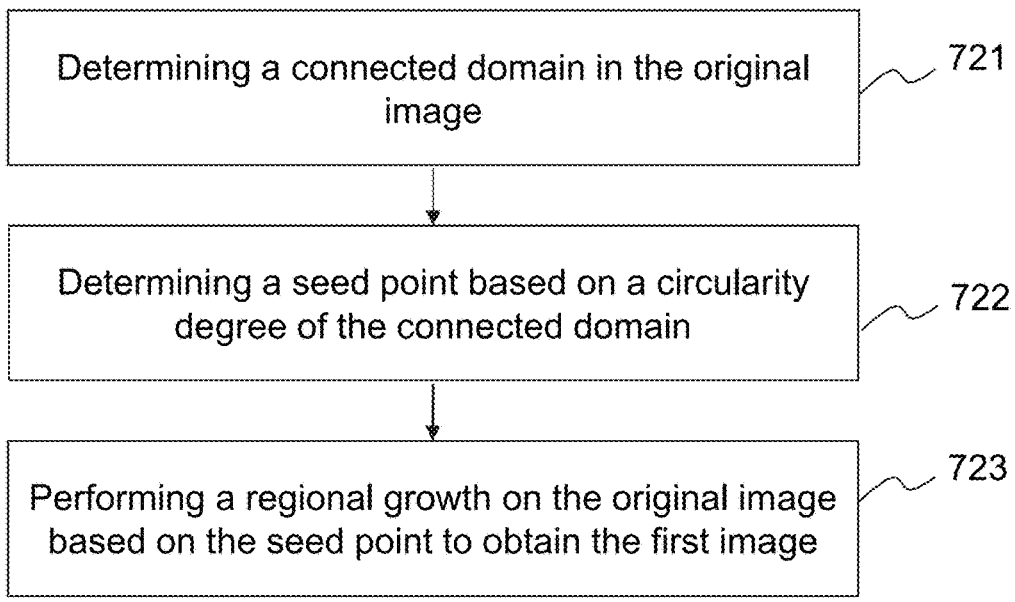
Figure 7D:
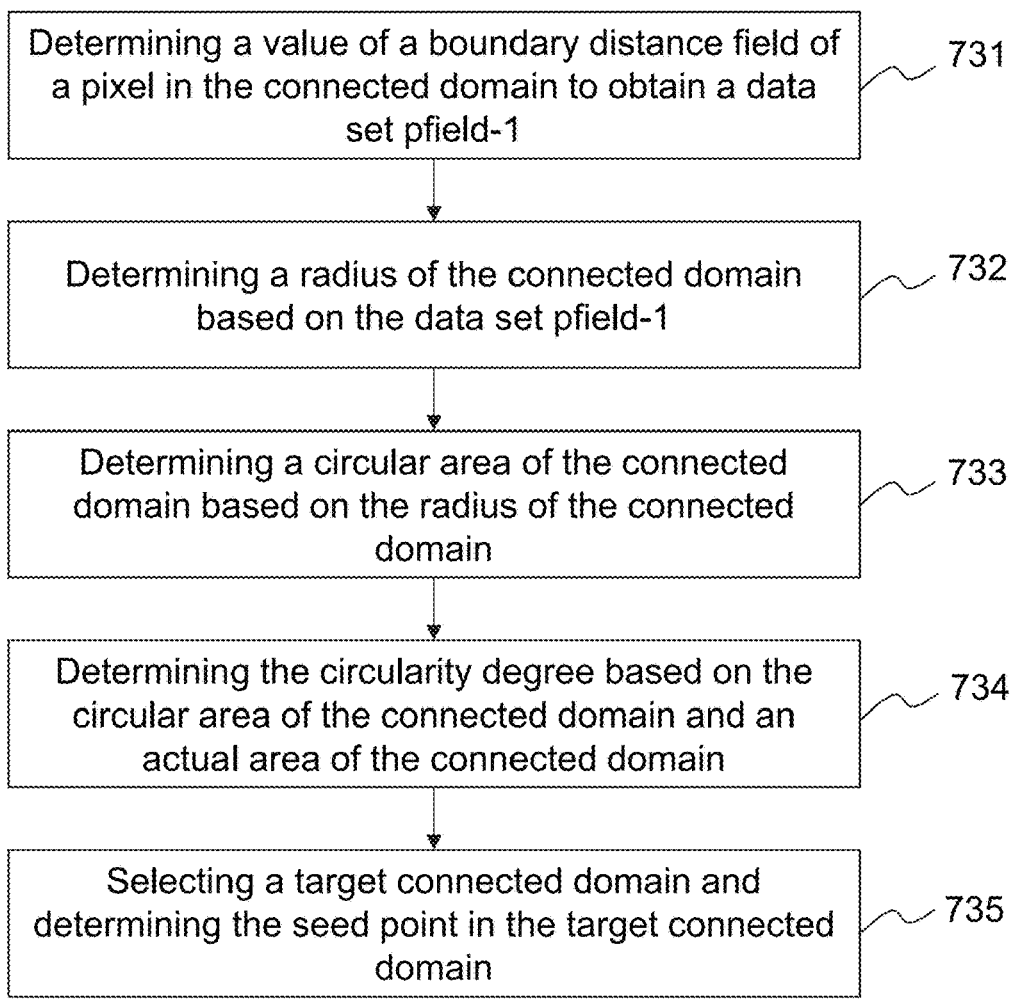
Figure 7E:
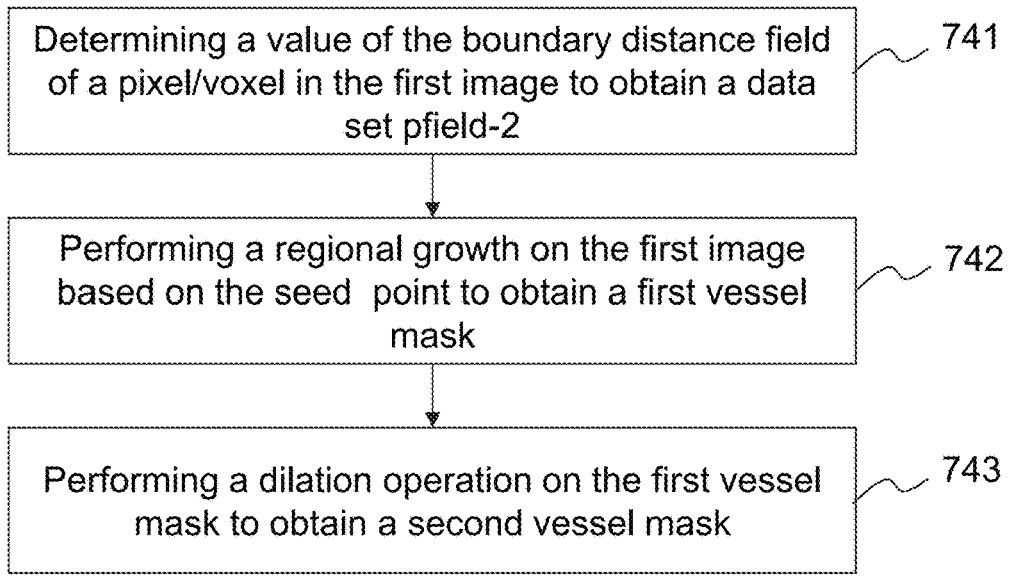
Figure 7F:
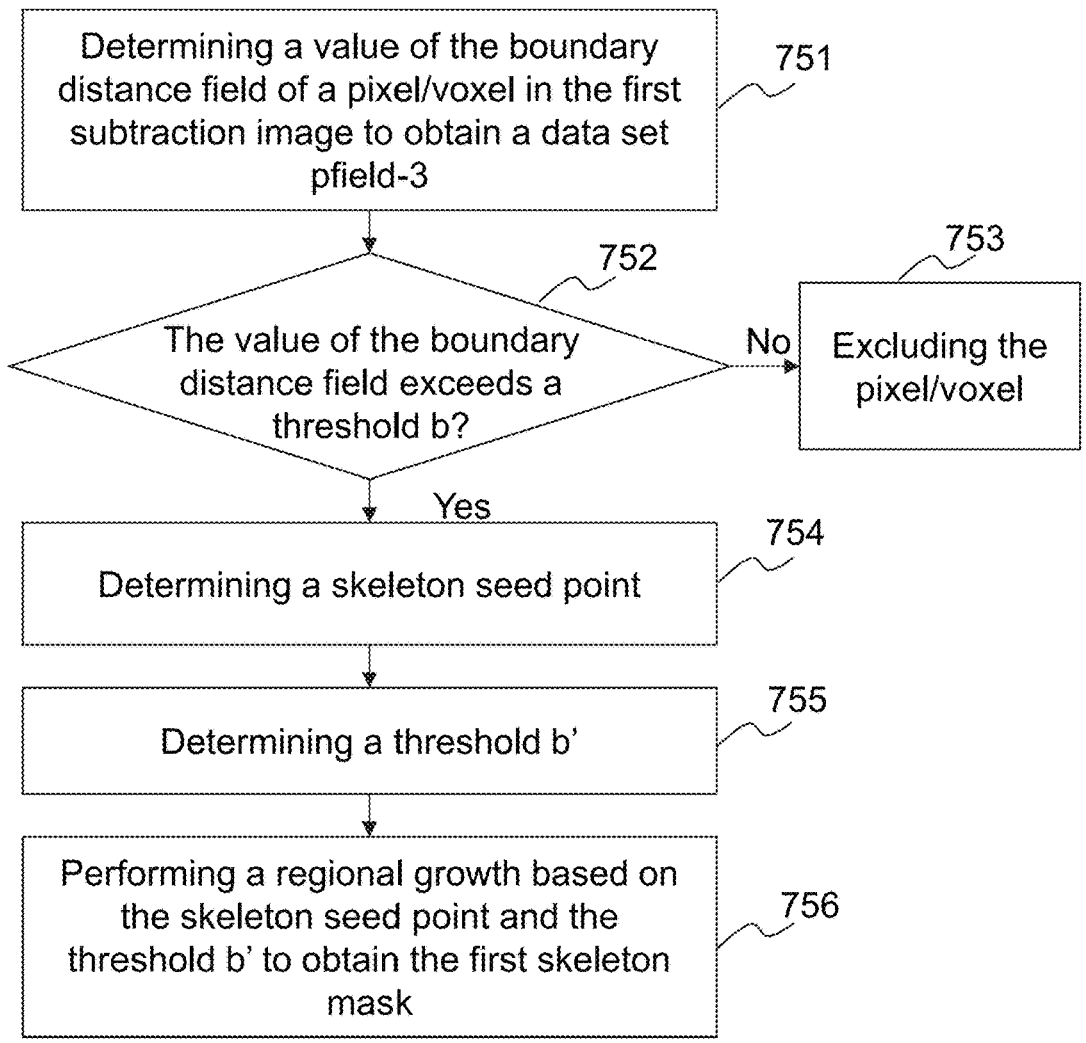
Figure 7G:
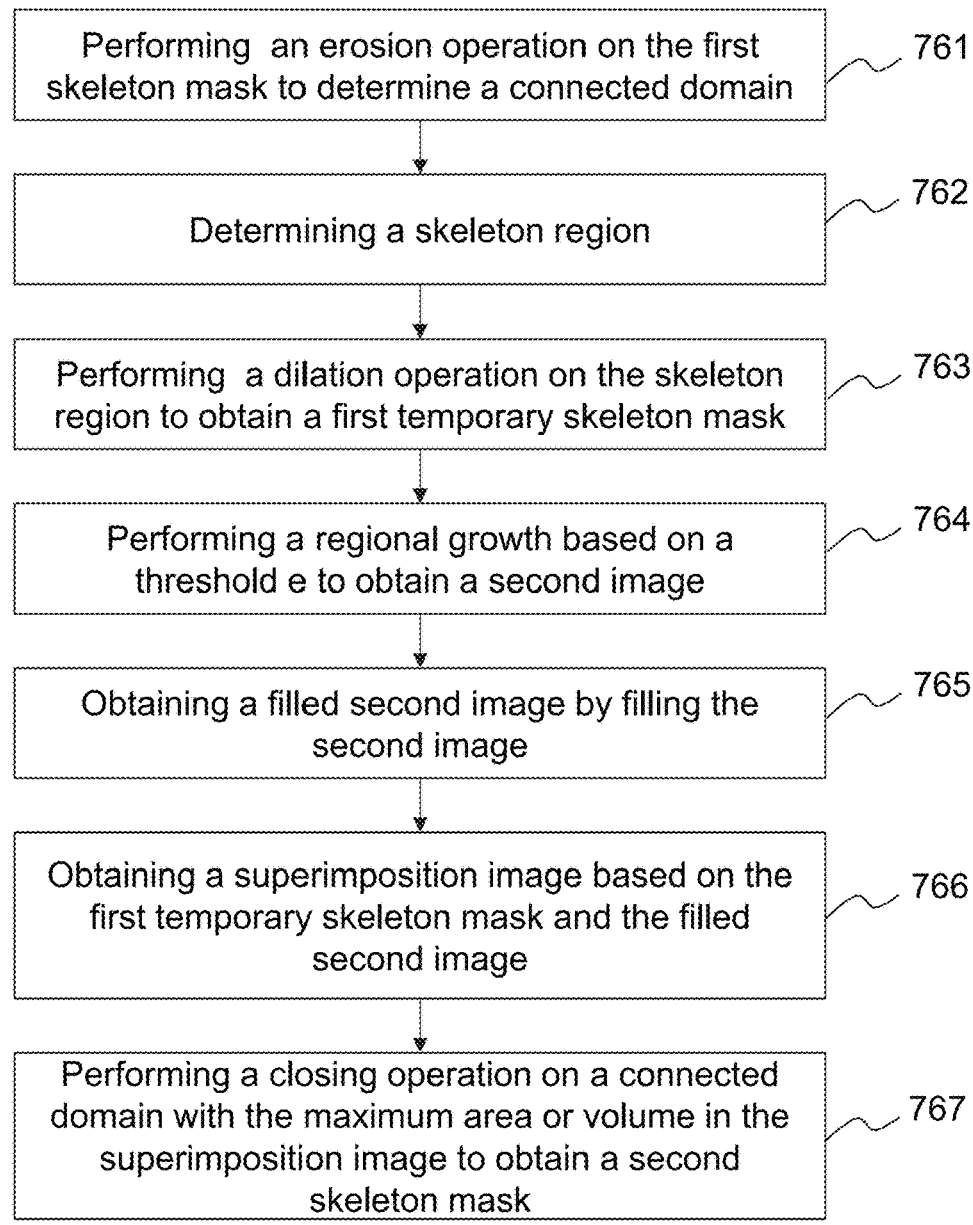
Figure 7H:
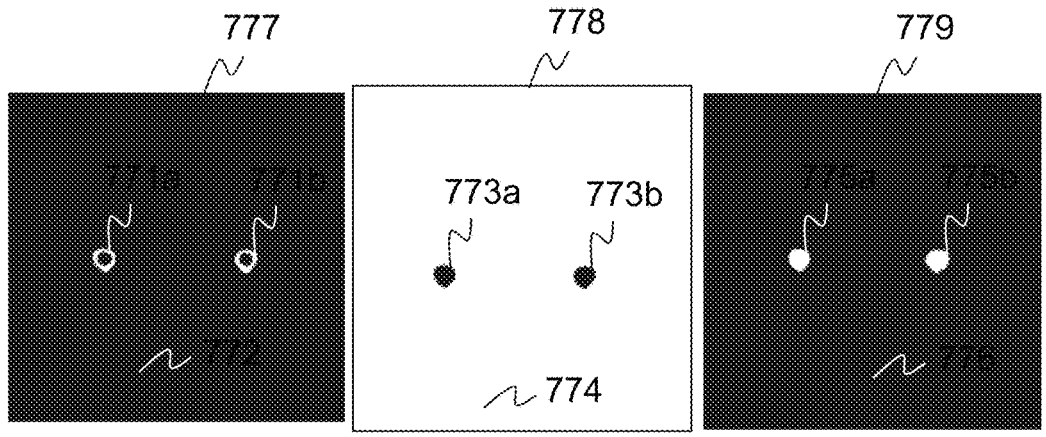

FIG. 6-A is a schematic diagram illustrating an exemplary vessel segmentation submodule 420 according to some embodiments of the present disclosure. In some embodiments, the target data may be vessel data. In some embodiments, according to the result of the reference data extraction in 512 and the method of extracting the target data in 513, the target data extraction unit 503 may further include a broken vessel segment extraction unit 603 and a vessel generation unit 604. In some embodiments, the vessel segmentation submodule 420 may include an image data input/output unit 601, a skeleton extraction unit 602, a broken vessel segment extraction unit 603, and a vessel generation unit 604.

In some embodiments, the image data input/output unit 601 and the image data input/output unit 501 may include the same or similar structures and functions; the skeleton extraction unit 602 and the reference data extraction unit 502 may include the same or similar structures and functions, and the skeleton data may be extracted to provide the reference data.

The broken vessel segment extraction unit 603 may extract broken vessel segments. The broken vessel segments may include a broken (or not connected) segment of a vessel formed during the image segmentation. In some embodiments, a vessel may include one or more broken vessel segments. A broken vessel segment may include one or more data relating to the vessel. Two or more broken vessel segments may include different amounts of vessel data. In some embodiments, the broken vessel segment extraction unit 603 may extract one, multiple, or all of the broken vessel segments of a vessel.

The vessel generation unit 604 may generate vessels. The vessel generation may be performed based on the image data, the skeleton data, and/or the data of the broken vessel segments. In some embodiments, the vessel generation unit 604 may generate vessels between two or more broken vessel segments based on the two or more broken vessel segments, and connect the two or more broken vessel segments by using one or more methods to generate one or more vessels.

FIG. 6-B is a flowchart illustrating an exemplary process for segmenting a vessel according to some embodiments of the present disclosure. In some embodiments, the process for vessel segmentation may further include obtaining original image data 611, extracting a skeleton 612, extracting broken vessel segments 613, and generating the vessel 614.

In 611, original image data may be obtained. 611 and 511 may be the same or similar. For example, the original image data obtained in 611 may be the same as the image data obtained in 511. The method for obtaining the original image data in 611 may be the same as the method in 511. The image data input/output unit 601 may perform 611.

In 612, skeleton data may be extracted. The method for extracting the skeleton data may be the same as or similar to the method for extracting the reference data in 512. In some embodiments, the extracted skeleton data may include one or more skeleton data. In some embodiments, the extracted skeleton data may also include one or more vessel data or data of other tissues. In some embodiments, the extraction of the skeleton data may be performed for one or more times. The skeleton extraction unit 602 may perform 612.

In 613, broken vessel segments may be extracted. In some embodiments, the extraction of the broken vessel segments may be performed based on the original image data obtained in 611 and/or the skeleton data extracted in 612. For example, one or more skeleton data may be removed from the original image data to obtain data of the broken vessel segments directly or indirectly. "Obtaining indirectly" may refer to that the data of the broken vessel segments may be obtained after the skeleton data is removed and the result after the removal of the skeleton data is further processed. In some embodiments, one or more operations (e.g., image erosion, dilation, increase or decrease in the number of the skeleton data) may be performed based on the skeleton data to obtain the processed skeleton data. Further, the processed skeleton data may be removed from the original image data to obtain the data of the broken vessel segments directly or indirectly. In some embodiments, the data of the broken vessel segments may be extracted based on a result of a first skeleton data extraction and a result of a second skeleton data extraction. For example, if the result of the first skeleton data extraction includes skeleton data and vessel data, and the result of the second skeleton data extraction includes skeleton data, the result of the second skeleton data extraction may be removed from the result of the first skeleton data extraction to obtain the data of the broken vessel segments directly or indirectly. The broken vessel segment extraction unit 603 may perform 613. For example, when extracting a broken vessel segment near an ilium (e.g., a region within a spatial distance threshold from the ilium), the broken vessel segment should be selected near a y coordinate of the ilium's position (e.g., a region within a distance threshold from the ilium in the y-direction), so that selection of crush bones near the vertebra may be avoided or decreased.

In 614, vessels may be generated. The vessel generation may be performed based on the data of the broken vessel segments extracted in 613. In some embodiments, the vessels may be generated between two or more broken vessel segments by using one or more algorithms. The vessel generation algorithm(s) may include one or more vessel segmentation techniques described above or any combination thereof. The vessel generation unit 604 may perform 614.

FIG. 7-A is a schematic diagram illustrating an exemplary skeleton extraction unit 602 according to some embodiments of the present disclosure. The skeleton extraction unit 602 may include a skeleton-vessel segmentation sub-unit 701, a boundary distance field calculation sub-unit 702, a vessel segmentation sub-unit 703, and a skeleton segmentation sub-unit 705.

The skeleton-vessel segmentation sub-unit 701 may segment a skeleton-vessel to obtain skeleton-vessel data. The skeleton-vessel data may include one or more skeleton data and one or more vessel data. In some embodiments, the skeleton-vessel data may include at least part of skeleton data, at least part of vessel data, and/or data of other tissues in the image data. For example, for image data of the lower limb, the skeleton-vessel data may include ilium data, femur data, tibia data, fibula data, and/or foot bone data, or the like, or a combination thereof; the skeleton-vessel data may also include data of an iliac artery, a femoral artery, a popliteal artery, a tibial artery, a fibular artery, an ankle artery, and/or a pedal artery, or the like, or a combination.

The boundary distance field calculation sub-unit 702 may calculate a boundary distance field of the image data and/or the skeleton-vessel data. The boundary distance field may include boundary distance value(s) of one or more pixels (or voxels) of the image. The boundary distance value(s) of the one or more pixels (or voxels) of the image may form a distance field. In some embodiments, the boundary distance value may refer to a distance from a pixel (or voxel) to a boundary. The boundary may be one or more pixels (or voxels) designated manually or automatically. For example, the boundary may refer to a boundary of a skeleton or a boundary of a vessel, etc.

The vessel segmentation sub-unit 703 may segment a vessel. The vessel segmentation may be performed based on the image data, the skeleton-vessel data, and/or the boundary distance field data. In some embodiments, the vessel segmentation sub-unit 703 may perform vessel segmentation on the boundary distance field of the skeleton-vessel data.

The skeleton segmentation sub-unit 704 may segment a skeleton. The skeleton segmentation may be performed based on the image data, the skeleton-vessel data, the boundary distance field data, and/or the vessel segmentation data. In some embodiments, the skeleton segmentation sub-unit 704 may perform skeleton segmentation on the boundary distance field of the skeleton-vessel data and the vessel segmentation data.

FIG. 7-B is a flowchart illustrating an exemplary process for extracting a skeleton according to some embodiments of the present disclosure. The process for extracting a skeleton may include obtaining a first image 711, obtaining a vessel mask 712, obtaining a first subtraction image 714, obtaining a first skeleton mask 715, and obtaining a second skeleton mask 716.

In 711, a first image may be obtained. The first image may include pixels (or voxels) corresponding to the skeleton-vessel data. In some embodiments, the first image may include one or more two-dimensional (or three-dimensional) connected domains of most of the vessels and the bone tissues. In some embodiments, the pixels (or voxels) in the first image and the data in the first reference data set in FIG. 5-A may be bijective. Obtaining of the first image may be performed based on the original image data obtained in 611. In some embodiments, the first image obtained in 711 may include at least part of the skeleton data and at least part of the vessel data in the image data. The first image may be obtained by using the one or more segmentation methods described above. For example, the first image may be obtained by using a threshold method. Specifically, a threshold $T_1$ may be set, and the data larger than the threshold $T_1$ may be extracted as skeleton-vessel data. In some embodiments, the threshold $T_1$ may be automatically, semi-automatically, or manually set. For example, the threshold may be automatically calculated or selected based on one or more operations. As another example, a user or operator may manually determine the threshold through a graphical user interface in the input/out device 140. As yet another example, a user or operator may, according to the automatically selected threshold, manually modify, change, or the like. Specifically, if the image data are CT values, CT values of the vessel may be relatively fixed, for example, in a range of 100 to 800 Hounsfield units (HU); while a CT value range of a skeleton may be relatively wide, some skeletal CT values may be smaller than the CT values of a vessel, and some skeletal CT values may be larger than the CT values of a vessel. Therefore, in some embodiments, a value smaller than the minimum CT value of the vessel may be selected as the threshold. The skeleton-vessel segmentation sub-unit 701 may perform 711.

In 712, a vessel mask may be obtained. In some embodiments, the vessel mask may be obtained through vessel segmentation. The vessel segmentation may be performed by using one or more image segmentation methods described above. For example, the vessel may be segmented by using a regional growth method. As another example, the vessel may be segmented by using a threshold method. A threshold $T_2$ may be automatically, semi-automatically, or manually set. For example, the threshold $T_2$ may be automatically set. As another example, a user or operator may manually determine the threshold through a graphical user interface in the input/out device 140. As another example, a user or operator may, according to the automatically selected threshold, manually modify, change, or the like. For example, the threshold $T_2$ may be determined as 2.5 (or 2.9) (a distance value). It should be noted that the values of the threshold $T_2$ listed above are for illustration purposes and are by way of example only and are not intended to limit the scope of the present disclosure as set forth. In some embodiments, the result of the vessel segmentation may be directly recorded as a vessel mask and used for subsequent operations. In some examples, the segmented vessel may be further processed, the result after processing may be recorded as a vessel mask and used for subsequent operations. In some embodiments, the operations may include a dilation operation or an erosion operation on the vessel (as shown in FIG. 7-E). The vessel segmentation sub-unit 703 may perform 712.

In 714, the vessel mask obtained in 712 may be subtracted from the first image to obtain a first subtraction image. In some embodiments, the first subtraction image may include a primary part of a skeleton tissue and a small number of small vessels, and a primary part of a vessel region (e.g., the vessel mask obtained in 712) may be subtracted through a subtraction operation. In some embodiments, the subtraction operation in 714 may refer to removing the pixels (or voxels) corresponding to the pixels (or voxels) in the vessel mask from the first image, and recording the remaining pixels (or voxels) as the first subtraction image. In some embodiments, the subtraction operation in 714 may refer to subtracting the values of the pixels (or voxels) in the first image from values of the corresponding pixels (or voxels) in the vessel mask and recording the subtracted results as the first subtraction image. The skeleton segmentation sub-unit 704 may perform 714.

In 715, a first skeleton mask may be obtained. In some embodiments, the first skeleton mask may be obtained by segmenting a skeleton. The skeleton segmentation may be performed based on the first subtraction image obtained in 714. The skeleton segmentation may be performed by using one or more image segmentation methods described above. For example, the skeleton may be segmented by using a threshold method in the first subtraction image. A threshold $T_3$ may be automatically, semi-automatically, or manually set. For example, the threshold $T_3$ can be automatically set by an operation of the data in the first subtraction image. As another example, a user or operator may manually determine the threshold through a graphical user interface in the input/out device 140. As another example, a user or operator may, according to the automatically selected threshold, manually modify, change, or the like. In some embodiments, the threshold $T_3$ may be determined as 1.5 (a distance value). In some embodiments, one or more seed points may be selected for the skeleton segmentation based on the threshold $T_3$. For example, a pixel (or voxel) including a distance value larger than 3.0 may be selected as the seed point to segment a skeleton. It should be noted that the value of the threshold $T_3$ and the distance value of the seed point described above are for illustration purposes and are by way of example only and are not intended to limit the scope of the present disclosure as set forth. In some embodiments, the result of the skeleton segmentation may be recorded as the first skeleton mask and used for subsequent operations. The skeleton segmentation sub-unit 704 may perform 715.

In 716, the first skeleton mask may be further processed to obtain a second skeleton mask. In some embodiments, the pixels (or voxels) in the first skeleton mask or the second skeleton mask and the data in the second reference data set in FIG. 5-A may be bijective. In some embodiments, through the process in 716, a part of a vessel that is mis-segmented in the first skeleton mask may be removed. For example, one or more pixels (or voxels) in the one or more vessels corresponding to the first skeleton mask may be recorded in the first skeleton mask and are mistaken for skeleton pixels (or voxels). In some embodiments, processing methods may include a morphological processing method, for example, dilation, erosion operations, or the like of the skeleton. In some embodiments, the process may be performed within a range of pixels (or voxels) in the first skeleton mask. For example, a dilation operation may be performed within a range of the pixels (or voxels) in the first skeleton mask. The dilation operation may refer to the use of a structural element including a certain size, moving it in the pixel (or voxel) of the image where the skeleton may be located, performing an "AND" operation of the structural element with the image it overlaps, and if the result of the "AND" operation is 0, pixel value(s) of the resulting image may be 0; otherwise 1. In some embodiments, through the dilation operation, the region where the skeleton may be located may be larger than the region before the operation. The skeleton segmentation sub-unit 704 may perform 716.

It should be noted that the above descriptions about the skeleton extraction unit and the process for extracting the skeleton are provided for illustration purposes, and should not be designated as the only practical embodiment. Each sub-unit may be implemented by one or more components, and the function of each sub-unit is not limiting. Each sub-unit may be added or omitted in specific scenarios. For persons having ordinary skills in the art, after understanding the general principle of the process for extracting the skeleton without departing the principle, may modify or change the forms or details of the particular practical ways and steps, and further make simple deductions or substitutions, or may make modifications or combinations of some steps without further creative efforts. For example, an image transformation sub-unit may be added to transform the image. As another example, steps 715 and 716 may be combined into one operation. A data storage operation may be added among 711 to 716 or thereafter. The data may be stored in the storage module 220.

FIG. 7-C is a flowchart illustrating an exemplary process for obtaining a first image according to some embodiments of the present disclosure. The process for obtaining a first image may include determining a connected domain in an original image 721, determining a seed point 722, and obtaining a first image 723. In some embodiments, the first image may be obtained by the skeleton-vessel segmentation sub-unit 701.

In 721, one or more connected domains in the original image may be determined. The original image may refer to an image corresponding to the original image data obtained in 611. In some embodiments, the original image may be a slice image (i.e., layer image) in a three-dimensional image. In some embodiments, the skeleton-vessel segmentation sub-unit 701 may determine one or more connected domains based on gray scale information. For example, the skeleton-vessel segmentation sub-unit 701 may determine pixels (or voxels) as a connected domain. Gray-scale values of the pixels (or voxels) may be within a predetermined range and/or the pixels (or voxels) may include adjacency relation.

In 722, a seed point may be determined. In some embodiments, the skeleton-vessel segmentation sub-unit 701 may determine the seed point based on a circularity degree of the connected domain. In some embodiments, the seed point may include a skeleton seed point and/or a vessel seed point. For example, the abdominal aorta may be approximately cylindrical in a three-dimensional space; the abdominal aorta may be represented by a round section in the slice image (i.e., layer image); the skeleton-vessel segmentation sub-unit 701 may determine a connected domain in the original image, and the connected domain may include a round section representing the abdominal aorta, and/or other irregular connected domains; the round section representing the abdominal aorta may be determined by comparing the circularity degrees of different connected domains for determining the seed point. In some embodiments, the circularity degree of the connected domain may refer to the ratio of the circle area S of the connected domain to the actual area S' of the connected domain. The circle area S of the connected domain may refer to the area of a circular region including a shape similar to the connected domain. In some embodiments, the skeleton seed point and the vessel seed point may be determined according to similar methods. FIG. 7-D shows examples of methods for determining a seed point.

In 723, a regional growth may be performed on the original image based on the seed point determined in 722 to obtain the first image. The first image may include one or more two-dimensional (or three-dimensional) connected domains including a large amount of vessels and skeletons. In some embodiments, the skeleton-vessel segmentation sub-unit 701 may perform the regional growth on the original image based on a threshold a. In some embodiments, if the original image is a three-dimensional image, in 723, the skeleton-vessel segmentation sub-unit 701 may perform a three-dimensional regional growth based on the seed point, and the obtained first image may include one or more three-dimensional connected domains. In some embodiments, the threshold a may be a threshold of a gray-scale value, for example, a gray-scale value of 200.

FIG. 7-D is a flowchart illustrating an exemplary process for determining a seed point according to some embodiments of the present disclosure. The process for determining a seed point may include determining a value of a boundary distance field 731, determining a radius of the connected domain 732, determining a circle area of the connected domain 733, determining a circularity degree 734, and determining a seed point 735. In some embodiments, the boundary distance field calculation sub-unit 702 may perform 731. In some embodiments, the determining the seed point may be performed by the skeleton-vessel segmentation sub-unit 701.

In 731, a value of a boundary distance field of one or more pixels in any of the connected domains in the above-mentioned slice image may be determined. The value of the boundary distance field may refer to a distance between the pixel and the nearest boundary point. In some embodiments, a boundary point may be a pixel in the boundary of the slice image. In some embodiments, the boundary point may be a pixel in the boundary of the connected domain. In some embodiments, the distance may be expressed as the number of pixels (i.e., a pixel width) between the pixel and the nearest boundary point. In some embodiments, the distance may be calculated by using a distance field formula as represented by Equation (1):

$$d_2 = \sqrt{(x-i)^2 + (y-j)^2} \qquad (1),$$

wherein $d_2$ may refer to the value of the two-dimensional boundary distance field of the pixel, (x, y) is the coordinate of the pixel in the connected domain, and (i, j) is the coordinate of the boundary point closest to the pixel. In some embodiments, values of the distance field of one or more pixels in the connected domain may be collected to generate a data set pfield-1. In some embodiments, this may mean that the smaller the value of the boundary distance field is, the closer the pixel is to the boundary point; the larger the value of the boundary distance field is, the farther the pixel is from the boundary point.

In 732, the radius r of the connected domain may be determined based on the data set pfield-1. In some embodiments, the skeleton-vessel segmentation sub-unit 701 may determine the radius r of the connected domain according to one or more standards. The standards may include a maximum value of the boundary distance, an average value, a median, and a modal number of values of two or more boundary distance, or the like. For example, the maximum value of the boundary distance field may be selected from the data set pfield-1 as the radius r of the connected domain.

In 733, the circle area S of the connected domain may be determined based on the radius r of the connected domain. In some embodiments, the circle area S may be determined based on the circle area formula $S = \pi r^2$.

In 734, the circularity degree c of the connected domain may be determined based on the circle area S and the actual area S' of the connected domain. In some embodiments, the circularity degree c may be determined based on the ratio of the circle area S and the actual area S' of the connected domain; that is, c=S/S'. In some embodiments, this may mean that the closer the circularity degree c is to 1, the closer the shape of the connected domain is to a circle. In some embodiments, the circularity degree(s) of one or more connected domains in the slice image may be determined based on the methods from 731 to 734. The circularity degrees may be collected to generate a data set dataset-1.

In 735, a seed point may be determined. In some embodiments, the skeleton-vessel segmentation sub-unit 701 may select one or more target connected domains based on the data set dataset-1. In some embodiments, the target connected domain may be a connected domain including the maximum circularity degree, or including a circularity degree close to 1. In some embodiments, the target connected domain may be automatically, semi-automatically, or manually determined. For example, in some embodiments, the skeleton-vessel segmentation sub-unit 701 may calculate absolute values of the difference values between all the circularity degrees and 1 in the data set dataset-1, and determine a connected domain with the minimum absolute value or a small absolute value as the target connected domain. As another example, a user or operator may completely manually determine a target connected domain through a graphical user interface in the input/out device 140. Alternatively, possible connected domains that are already determined (e.g., determined by the skeleton-vessel segmentation sub-unit 701) may be presented to a user or operator, and then the user or operator may select a target connected domain through a graphical user interface in the input/out device 140. This process of selecting a target connected domain may be called semi-automatic selection. As another example, a user or operator may, according to the automatically selected target connected domain, manually modify, change, or the like.

In some embodiments, the skeleton-vessel segmentation sub-unit 701 may determine one or more pixels in the target connected domain as the seed point(s). In some embodiments, the seed points may be automatically, semi-automatically, or manually determined. In some embodiments, the skeleton-vessel segmentation sub-unit 701 may automatically determine a seed point according to one or more standards, for example, determining a pixel including the maximum value or a large value of the boundary distance field in the target connected domain as the seed point. As another example, a user or operator may completely manually determine the seed point through a graphical user interface in the input/out device 140. Alternatively, the one or more possible seed points that are already determined (e.g., determined by the skeleton-vessel segmentation sub-unit 701) may be presented to a user or operator, and then the user or operator may select a target seed point through a graphical user interface in the input/out device 140. This process of determining the seed point may be called semi-automatic determination. As another example, a user or operator may, according to the automatically selected threshold, manually modify, change, or the like. In some embodiments, 731 to 735 may be performed in the slice image (i.e., layer image or two-dimensional image), the seed point determined in 735 may be a pixel in the two-dimensional image, and the seed point may correspond to a voxel in the three-dimensional image.

FIG. 7-E is a flowchart illustrating an exemplary process for obtaining a vessel mask according to some embodiments of the present disclosure. The process for obtaining a vessel mask may include determining a value of a boundary distance field 741, obtaining a first vessel mask 742, and obtaining a second vessel mask 743. In some embodiments, the boundary distance field calculation sub-unit 702 may perform 741. In some embodiments, the first vessel mask and the second vessel mask may be obtained by the vessel segmentation sub-unit 703.

In 741, values of the boundary distance field of the pixels/voxels in the first image may be determined. The values of the boundary distance field may be collected to generate a data set pfield-2. In some embodiments, a value of the boundary distance field may refer to a distance from a pixel/voxel to the nearest boundary point. In some embodiments, the boundary point may be a pixel/voxel in the boundary of the first image. In some embodiments, the distance may be expressed as the number of pixels/voxels (i.e., pixel/voxel width) between the pixel/voxel and the nearest boundary point. In some embodiments, as for a two-dimensional pixel, the distance may be calculated by using Equation (1). In some embodiments, for a three-dimensional voxel, the distance may be calculated by a distance field formula as represented by Equation (2):

$$d_3 = \sqrt{(x-i)^2 + (y-j)^2 + (z-k)^2} \qquad (2),$$

wherein $d_3$ may refer to the value of the three-dimensional boundary distance field of the pixel, (x, y, z) may refer to the coordinate of one voxel in the first image, and (i, j, k) may refer to the coordinate of the boundary point closest to the voxel. In some embodiments, this may mean that the smaller the value of the boundary distance field is, the closer the pixel/voxel is to the boundary point; the larger the value of the boundary distance field is, the farther the pixel/voxel is from the boundary point. In some embodiments, the boundary distance field values of all the pixels/voxels in the first image may form an image of a boundary distance field. The pixels/voxels in the image of the boundary distance field and the pixels/voxels in the first image may be bijective.

In 742, a first vessel mask may be obtained. In some embodiments, the skeleton-vessel segmentation sub-unit 701 may perform a two-dimensional regional growth or a three-dimensional regional growth on the first image based on a seed point. In some embodiments, the seed point may be the seed point determined in 722 (e.g., the seed point determined in 735). In some embodiments, the operation of regional growth may be performed based on a threshold. In some embodiments, the regional growth may be performed in the image of the boundary distance field. The threshold may be determined based on the values of the boundary distance field, for example, a value of the boundary distance field larger than 3.0 as the threshold. In some embodiments, the radius of the vessel in the first image may decrease and be closer to the bone along the the vessel. This may mean that the closer the vessel is to a boundary point of the first image, the closer the vessel is to the bone, the smaller the vessel radius is, and the smaller the value of the boundary distance field of the pixel/voxel is. Therefore, the following may be controlled by determining the threshold: the vessel does not grow to the skeleton, and a vessel with a small radius does not grow. The first vessel mask may be obtained after performing the regional growth on the first image. The first vessel mask may include pixels/voxels corresponding to vascular tissues including large radii.

In 743, a dilation operation may be performed on the first vessel mask to obtain a second vessel mask. In some embodiments, the vessel segmentation sub-unit 703 may perform the dilation operation by using a structural element. The structural element may include a certain size, for example, the width of 4 pixels/voxels. The second vessel mask may be obtained after the dilation operation. The second vessel mask may include pixels/voxels representing the vascular tissue. Compared to the first vessel mask, the second vessel mask may include more vascular tissues. In some embodiments, the second vessel mask may include most of the vascular tissue in the first image.

FIG. 7-F is a flowchart illustrating an exemplary process for obtaining a first skeleton mask according to some embodiments of the present disclosure. The process for obtaining the first skeleton mask may include determining a value of the boundary distance field 751, determining whether the value of the boundary distance field exceeds a threshold 752, excluding a pixel/voxel 753, determining a skeleton seed point 754, determining a threshold 755, and obtaining a first skeleton mask 756. In some embodiments, the boundary distance field calculation sub-unit 702 may perform 751. In some embodiments, the first skeleton mask may be obtained by the skeleton segmentation sub-unit 704.

In 751, values of the boundary distance field of the pixels/voxels in the first subtraction image may be determined. The values of the boundary distance field values may be collected to generate a data set pfield-3. In some embodiments, for a two-dimensional pixel, the value of the boundary distance field may be calculated by using Equation (1). In some embodiments, for a three-dimensional voxel, the value of the boundary distance field may be calculated by using Equation (2).

In 752, whether the value of the boundary distance field exceeds a threshold b may be determined. In some embodiments, the threshold b may be a value of the boundary distance field larger than 3.0. In some embodiments, the threshold b may be a default threshold of the data processing system 130 or a threshold set based on the result of the skeleton segmentation, or a threshold set by a user or operator through a graphical user interface in the input/out device 140.

In 753, the pixel/voxel including a value of the boundary distance field smaller than the threshold b may be excluded. This may mean that the pixel/voxel including a value of the boundary distance field smaller than the threshold b may not be determined as the skeleton seed point.

In 754, a skeleton seed point may be determined. In some embodiments, the pixel/voxel including a value of the boundary distance field larger than the threshold b may be determined as the skeleton seed point. Since the vessel, the mask has been subtracted from the first subtraction image and the vessel mask may include the pixels/voxels with large values of the boundary distance field that may represent the vascular tissues, the pixels/voxels having large values of the boundary distance field in the first subtraction image may represent skeleton tissue.

In 755, a threshold b' may be determined. In some embodiments, the threshold b' may refer to the threshold used in the regional growth in 756. In some embodiments, the threshold b' may include a threshold of gray scale information and/or a threshold of the boundary distance field. In some embodiments, the gray scale information may include a texture structure, a gray-scale value, an average grayscale, intensity, a color saturation, contrast, brightness, or the like, or a combination thereof. For example, the threshold b' may be a gray-scale value larger than 500, or a value of a boundary distance field greater than 1.5. In some embodiments, the threshold may be automatically, semi-automatically, or manually determined. For example, the skeleton segmentation sub-unit 704 may automatically determine the threshold b' based on one or more standards. As another example, a user or operator may completely manually input the threshold b' through a graphical user interface in the input/out device 140. Alternatively, one or more possible thresholds that are already determined (e.g., determined by the skeleton segmentation sub-unit 704) may be presented to a user or operator, and then the user or operator may select a threshold b' through a graphical user interface in the input/out device 140. This process of determining the threshold may be called semi-automatic determination. As yet another example, a user or operator may, according to the automatically selected threshold b', manually modify, change, or the like.

In 756, the regional growth may be performed based on the skeleton seed point determined in 754 and the threshold b' determined in 755 to obtain a first skeleton mask. In some embodiments, the regional growth may be performed based on the gray scale information of the first subtraction image, or based on the values of the boundary distance field of the pixels/voxels in the first subtraction image. Accordingly, the threshold b' may be a threshold of gray scale information or a threshold of the value of the boundary distance field. The obtained first skeleton mask may include pixels/voxels representing skeletons, and a small amount of other pixels/voxels representing non-skeletons (e.g., vessels).

FIG. 7-G is a flowchart illustrating an exemplary process for obtaining a second skeleton mask according to some embodiments of the present disclosure. The process for obtaining the second skeleton mask may include determining a connected domain 761, determining a skeleton region 762, obtaining a first temporary skeleton mask 763, obtaining a second image 764, filling a second image 765, obtaining a superimposition image 766, and obtaining a second skeleton mask 767. In some embodiments, the boundary distance field calculation sub-unit 702 may perform 761. In some embodiments, the second skeleton mask may be obtained by the skeleton segmentation sub-unit 704.

In 761, the erosion operation may be performed on the first skeleton mask to determine a connected domain. The erosion operation may refer to the use of a structural element including a certain size, moving it in the pixel (or voxel) of the image where the skeleton may be located, performing an "AND" operation of the structural element with the image it overlaps; and if the result of the "AND" operation is 1, pixel values of result image may be 1, otherwise 0. Since the first skeleton mask may include pixels/voxels representing a vessel, one or more pixels/voxels representing the vessel may be removed through the erosion operation. In some embodiments, the pixels/voxels representing the vessel in the first skeleton mask may be close to the pixels/voxels representing the skeleton and may be difficult to distinguish from each other, and connection part of the vessel, and the skeleton may be broken through the erosion operation. In some embodiments, one or more pixels/voxels representing the skeleton may be missing through the erosion operation. In some embodiments, the skeleton segmentation sub-unit 704 may perform the erosion operation by using a structural element. The structural element may include a certain size, for example, a width of 5 pixels/voxels. In some embodiments, one or more connected domains may be obtained after the erosion operation.

In 762, a skeleton region may be determined. In some embodiments, the skeleton segmentation sub-unit 704 may determine one or more skeleton regions based on the connected domain determined in 761. In some embodiments, the skeleton region may be automatically, semi-automatically, or manually determined. For example, the skeleton region may be automatically determined according to one or more standards. The standards may include selecting a connected domain including a maximum area or a maximum volume. As another example, a user or operator may manually determine a skeleton region through a graphical user interface in the input/out device 140. Alternatively, one or more possible skeleton regions that are already determined (e.g., determined by the skeleton segmentation sub-unit 704) may be presented to a user or operator, and the user or operator may select a skeleton region through a graphical user interface in the input/out device 140. This process of determining the skeleton region may be called semi-automatic determination. As yet another example, a user or operator may, according to the automatically selected skeleton region, manually modify, change, or the like.

In 763, the dilation operation may be performed on the skeleton region to obtain a first temporary skeleton mask. In some embodiments, the skeleton segmentation sub-unit 704 may perform the dilation operation by using a structural element. The structural element may include a certain size, for example, a width of 5 pixels/voxels. By the dilation operation, the obtained first temporary skeleton mask may restore one or more pixels/voxels representing the skeleton that are missing due to the erosion process in 761. In some embodiments, the first temporary skeleton mask may include pixels/voxels representing the skeleton, while pixels/voxels representing the vessel may be removed.

In 764, a second image may be obtained. In some embodiments, the regional growth may be performed on the original image based on one or more seed points and a threshold e to obtain the second image. In some embodiments, the seed point may be the seed point determined in 722. In some embodiments, the threshold e may be smaller than the threshold a used in 723. In some embodiments, since gray-scale information of the skeleton is below the skeleton tissue, etc., the threshold a used in 723 may result in missing of part of skeleton information in the first image. Using a threshold e smaller than the threshold a to perform the regional growth may supplement the missing skeleton information. Compared to the first image, the second image may include more skeleton information.

In 765, the second image may be filled to obtain a filled second image. Filling the second image may refer to filling the connected domain representing the skeleton region in the second image. In some embodiments, the skeleton segmentation sub-unit 704 may fill the connected domain in the second image layer by layer. For example, the skeleton segmentation sub-unit 704 may select a slice image (i.e., layer image) of the second image to perform the regional growth on background region based on the result of the first temporary skeleton mask to obtain a binary image of the background region (e.g., the gray-scale value of the background region may be 1, the gray-scale value of the connected domain in the skeleton region may be 0, as shown in FIG. 7-H). Then, the skeleton segmentation sub-unit 704 may perform a reverse operation on the binary image, for example, determining the gray-scale value of the background region as 0, determining the gray-scale value of the connected domain in the skeleton region as 1, so that filling of the skeleton region in the slice image may be performed (as shown in FIG. 7-H). Similarly, the filling operation may be performed on the second image layer by layer to obtain the filled second image. An example of filling the skeleton region is shown in FIG. 7-H.

In 766, a superimposition image may be obtained based on the first temporary skeleton mask and the filled second image. In some embodiments, the skeleton segmentation sub-unit 704 may perform superimposition of the first temporary skeleton mask and the filled second image. In some embodiments, the superimposition may refer to superimposition of the first temporary skeleton mask and the corresponding connected domain in the filled second image. In some embodiments, the superimposition operation may refer to adding up the values of corresponding pixels/voxels. In some embodiments, possible voids or missing skeleton edges may be filled through the superimposition operation. In some embodiments, great gaps or voids in the skeleton region may be filled through the superimposition operation. In some embodiments, there may be several gaps or voids with small pixel/voxel widths between the connected domains in the superimposition image, and the skeleton segmentation sub-unit 704 may further perform a closing operation on the superimposition image. The closing operation may refer to performing dilation on the superimposition image by using a first structural element and then performing erosion on dilated superimposition image by using a second structural element. The first structural element and the second structural element may include the same size or different sizes.

In 767, the closing operation may be performed in the connected domain including a maximum volume of the superimposition image to obtain a second skeleton mask. In some embodiments, the skeleton segmentation sub-unit 704 may extract the connected domain including the maximum area or the maximum volume in the superimposition image. In some embodiments, the connected domain including the maximum volume may correspond to a skeleton region. In the skeleton region, a mis-extracted vessel may be already removed, and one or more pixels/voxels representing the skeleton may also be removed. The closing operation may refer to performing dilation on the superimposition image by using a first structural element and then performing erosion on dilated superimposition image by using a second structural element. The first structural element and the second structural element may include the same size or different sizes (e.g., a width of 10 pixels/voxels). In some embodiments, gaps or voids including small sizes (e.g., a width of several pixels/voxels) in the skeleton region may be filled through the closing operation.

FIG. 7-H is a schematic diagram illustrating an exemplary filling operation on a skeleton region according to some embodiments of the present disclosure. An image 777 may represent a binary image of a slice image. The gray values of the edges of the skeleton regions 771a and 771b may be 1, the skeleton regions 771a and 771b may include hollow structures, and the gray-scale value of a background region 772 is 0. An image 778 may represent a binary image of an intermediate result of the filling operation. In the image 778, the regional growth may be performed on the background region 774. For example, a seed point may be selected in the edges of the skeleton regions 771a or 771b of the image 777, and then the regional growth may be performed on the background region 774. The gray-scale value of the background region 774 may be 1, and the gray-scale value of a connected domain where the skeleton regions 773a and 773b are located may be 0. The image 779 may represent a binary image of the result of the filling operation. The image 779 may be obtained by performing the reverse operation on the image 778, for example, the pixels/voxels including a gray-scale value of 1 is modified to include a gray-scale value of 0, and the pixels/voxels including a gray-scale value of 0 is modified to include a gray-scale value of 1. The skeleton regions 775a and 775b in the image 779 have been filled through such processes.

Figure 8:
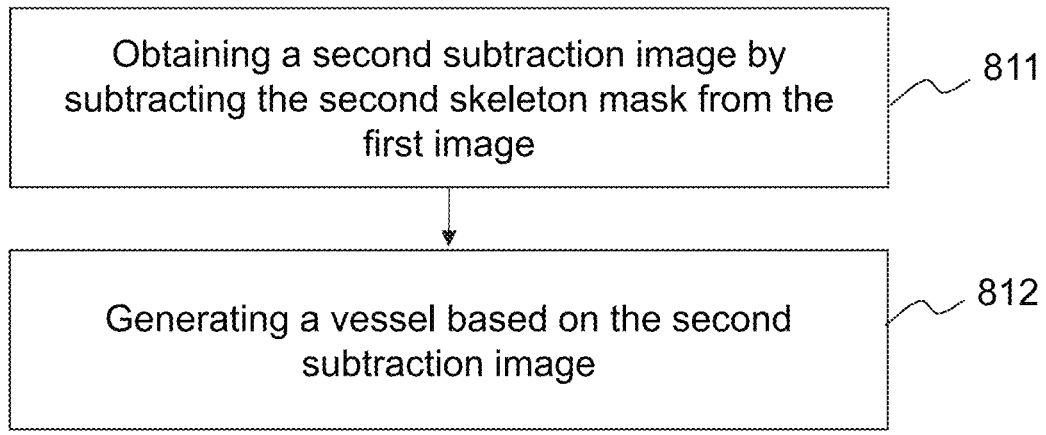
FIG. 8 is a flowchart illustrating an exemplary process for generating a vessel according to some embodiments of the present disclosure.

FIG. 8 is a flowchart illustrating an exemplary process for generating a vessel according to some embodiments of the present disclosure. The process for generating the vessel may include obtaining a second subtraction image 811 and generating a vessel 812.

In 811, a second subtraction image may be obtained. In some embodiments, the second subtraction image and the data of the broken vessel segment described in FIG. 6-B may be bijective. In some embodiments, the second subtraction image and the data in the frame data set of FIG. 5-B may be bijective. In some embodiments, the second subtraction image may include one or more connected domains. The connected domain may include broken vessel segments and/or skeleton fragments. In some embodiments, the broken vessel segment extraction unit 603 may perform 811. In some embodiments, the broken vessel segment extraction unit 603 may subtract the second skeleton mask from the first image to obtain a second subtraction image. In some embodiments, the subtraction operation may refer to removing pixels/voxels corresponding to the second skeleton mask from the first image, and the remaining pixels/voxels in the first image are recorded as a second subtraction image. In some embodiments, values of the pixels/voxels in the first image may be different from values of the corresponding pixels/voxels in the second skeleton mask. The subtraction operation may refer to subtracting the values of the corresponding pixels/voxels in the second skeleton mask from the values of the pixels/voxels in the first image, and the obtained values of the pixels/voxels may be recorded as a second subtraction image. In some embodiments, since the methods, processes, or parameters used are different, the obtained data in the broken vessel segment may include one or more data of skeleton fragments. The skeleton fragments may refer to data of residual skeleton tissues produced at the edge of the vessel due to the skeleton segmentation during processing.

In 812, a vessel may be generated based on a second subtraction image. In some embodiments, the vessel generation unit 604 may perform 812. In some embodiments, the vessel may be generated between two or more broken vessel segments (e.g., the connected domain obtained in 811) by using one or more algorithms. The vessel generation algorithms may include one or more vessel segmentation methods described above and any combination thereof. The detailed description of the vessel generation is as shown in FIGS. 10-A to 10-E.

Figure 9:
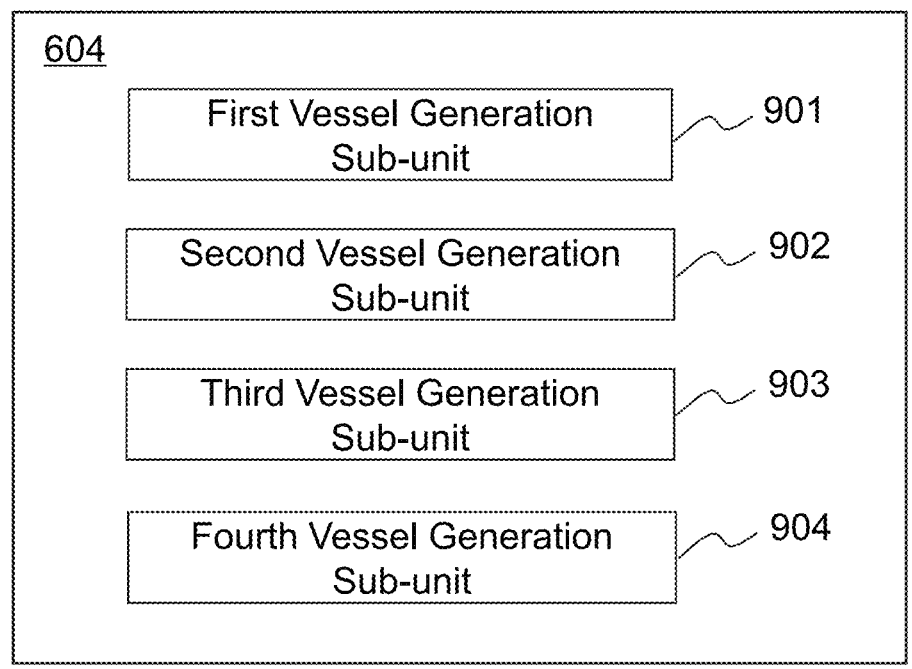
FIG. 9 is a schematic diagram illustrating an exemplary vessel generation unit according to some embodiments of skeleton the present disclosure.
Figure 10A:
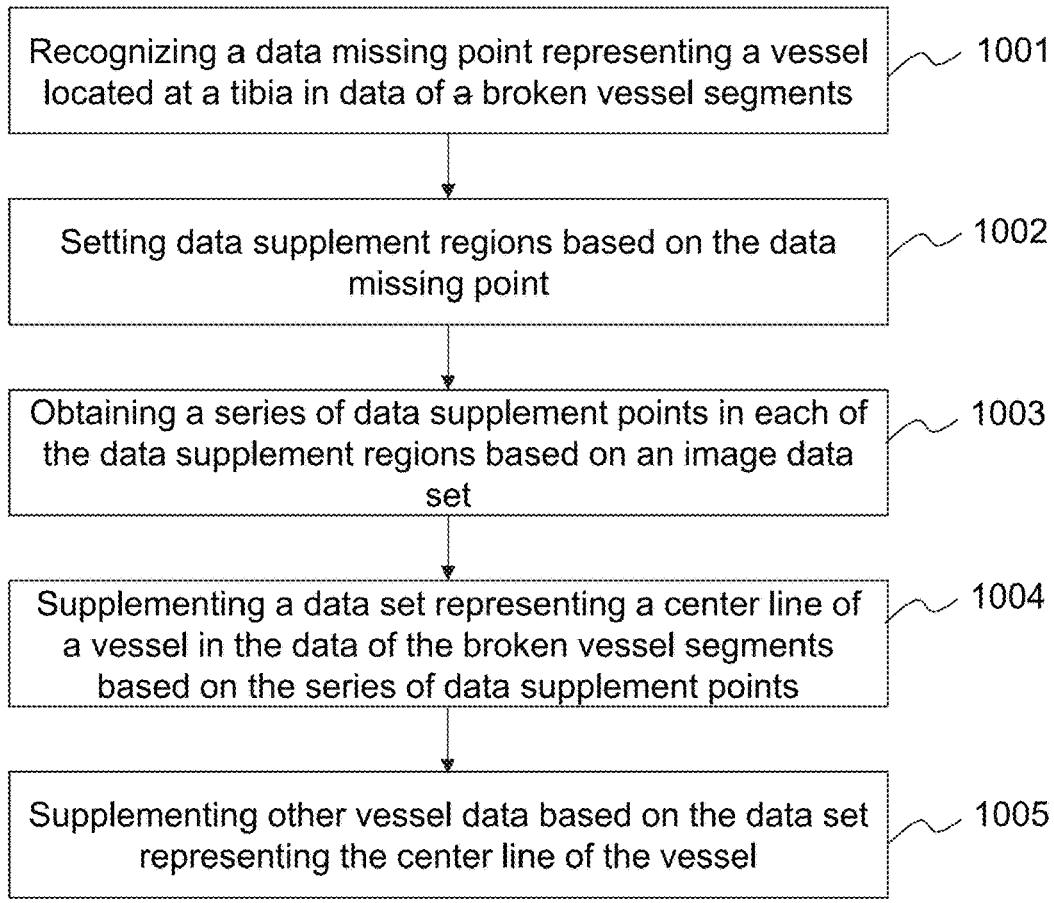
FIG. 10-A is a flowchart illustrating an exemplary process for supplementing tibia vessel data according to some embodiments of the present disclosure.
Figure 10B:
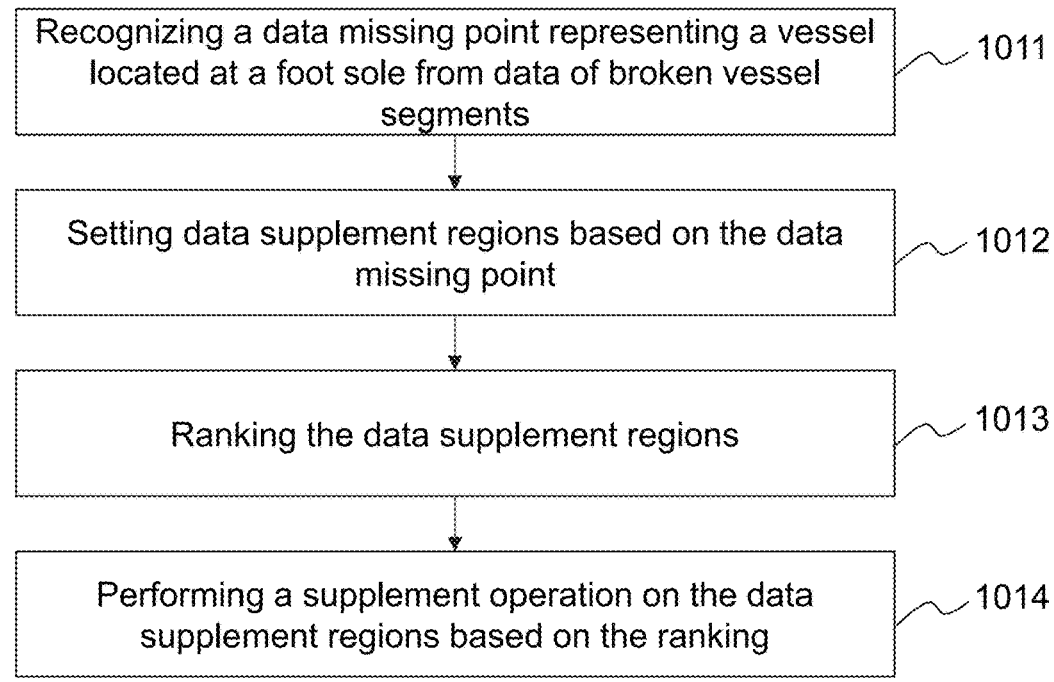
Figure 10C:
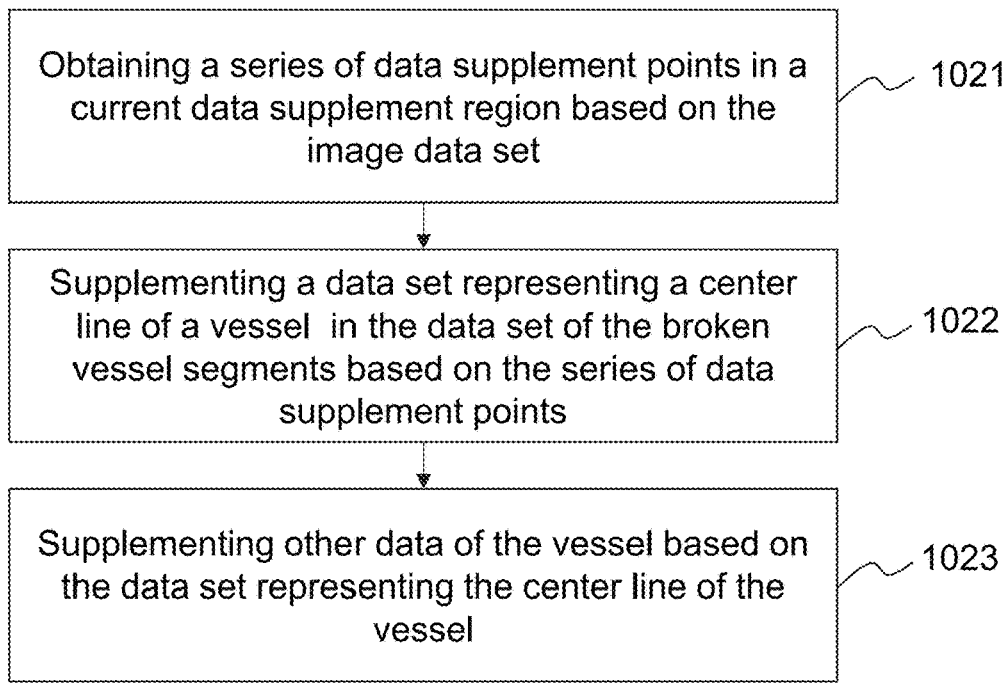
Figure 10D:
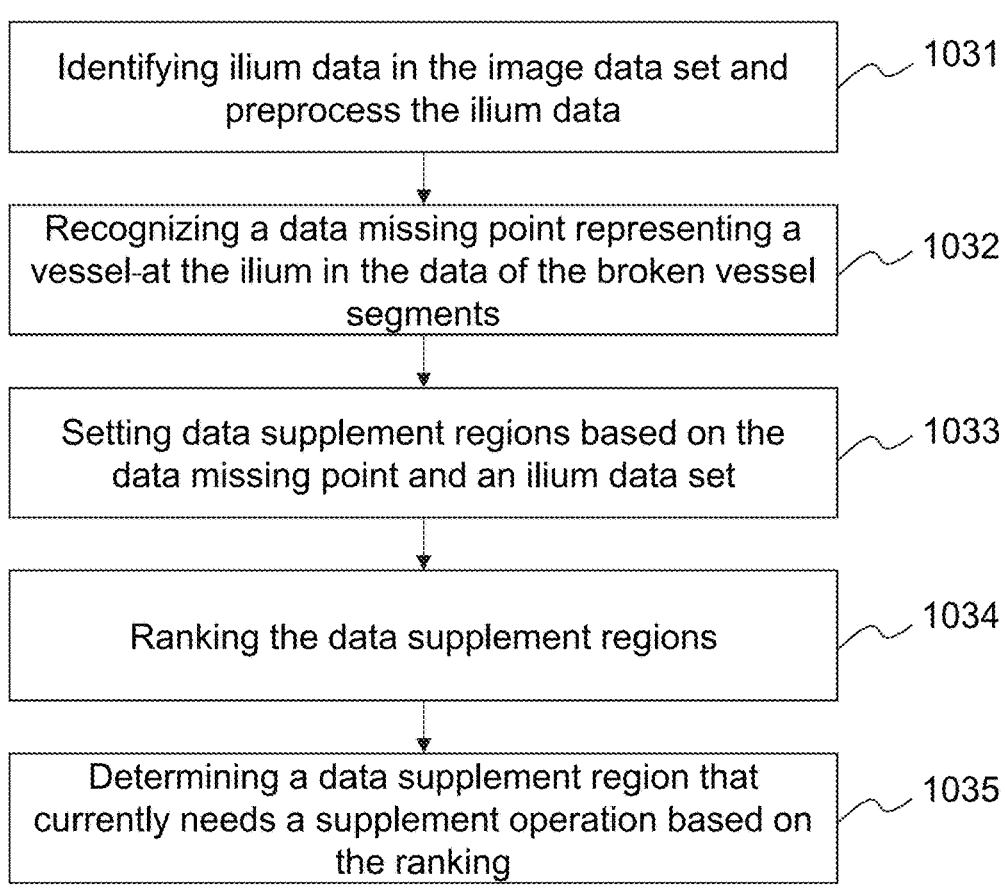
Figure 10E:
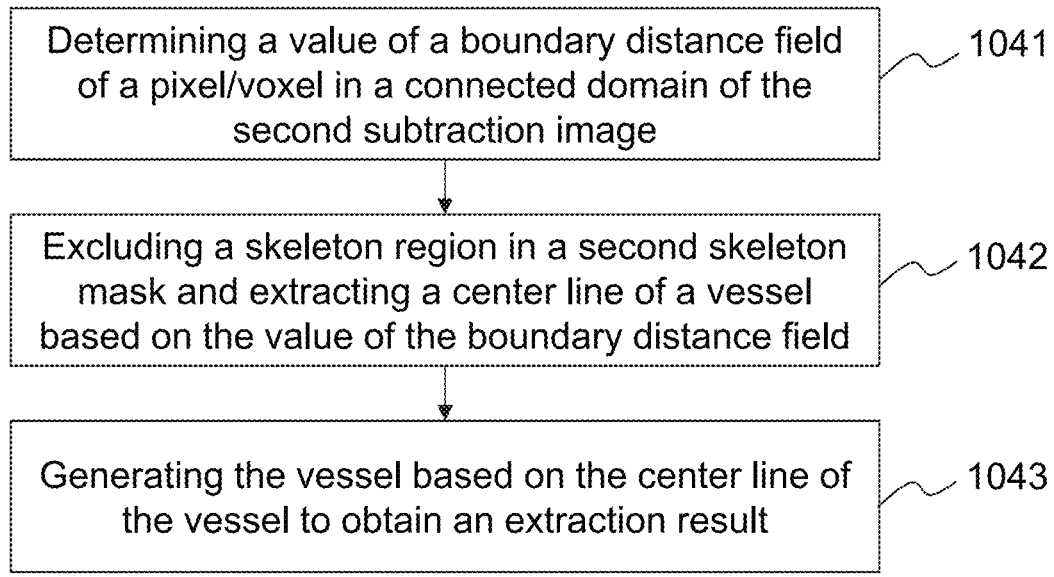

FIG. 9 is a schematic diagram illustrating an exemplary vessel generation unit 604 according to some embodiments of skeleton the present disclosure. In some embodiments, the vessel generation unit 604 may further include a first vessel generation sub-unit 901, a second vessel generation sub-unit 902, a third vessel generation sub-unit 903, and a fourth vessel generation sub-unit 904. The first vessel generation sub-unit 901 may generate a vessel based on a site where a vessel of a tibia may break. The detailed process for generating the vessel of the tibia is shown in FIG. 10-A. The second vessel generation sub-unit 902 may generate a vessel based on a site where a vessel of a foot may break. The detailed flow of generating the vessel of the foot is shown in FIG. 10-B. The third vessel generation sub-unit 903 may generate a vessel based on a site where a vessel of an ilium may break. The detailed process for generating the vessel of the ilium is shown in FIG. 10-D. The fourth vessel generation sub-unit 904 may generate a corresponding vessel based on a site where the corresponding vessel may break. The detailed process for generating the vessel is shown in FIG. 10-E. In some embodiments, the fourth vessel generation sub-unit 904 may generate a vessel of a tibia, a vessel of a foot, a vessel of an ilium, and/or any other vessel other than the vessel of the tibia, the vessel of the foot, and the vessel of the ilium.

It should be noted that the above descriptions about the vessel generation module are provided for illustration purposes, and should not be designated as the only practical embodiment. Each submodule may be implemented by one or more components, and the function of each submodule is not limiting. Each submodule may be added or omitted in specific scenarios. For persons having ordinary skills in the art, after understanding the general principle of the process for generating the vessel, without departing the principle, may modify or change the forms or details of the particular practical ways and steps, and further make simple deductions or substitutions, or may make modifications or combinations of some steps without further creative efforts. For example, the first vessel generation sub-unit 901, the second vessel generation sub-unit 902, the third vessel generation sub-unit 903, and/or the fourth vessel generation sub-unit 904 may be combined into one unit.

FIG. 10-A is a flowchart illustrating an exemplary process for supplementing tibia vessel data according to some embodiments of the present disclosure. Supplementing the tibia vessel data may be performed by the first vessel generation sub-unit 901. In 1001, data missing points representing the vessel of the tibia between the broken vessel segments may be identified based on vessel broken data. For example, the data missing points of the vessels may be a site between the broken vessel segments in the image data (e.g., the image data of a crus site obtained in 611), including but not limited to a vessel segment that should be connected and false positive data.

In 1002, the first vessel generation sub-unit 901 may determine data supplement regions based on the data missing points representing the vessel of the tibia obtained in 1001. In some embodiments, the data supplement region may refer to a vessel segment that is blocked by the skeleton and should have been connected. In some embodiments, the first vessel generation sub-unit 901 may extract a bone section of every layer to form a histogram, based on the skeleton data (for example, the skeleton data extracted by the skeleton extraction unit 602). In some embodiments, the horizontal axis of the histogram may represent the number of layers, and the longitudinal axis of the histogram may represent the size of the bone section. In some embodiments, the number of layers may be determined along the direction perpendicular to the horizontal axis. Along the direction of the knee to foot, a position where the size of the bone section nearest to the foot in the histogram is maximum may be considered as an approximate position where the vessel of the tibia may be missing. Near this position (e.g., a region within a spatial distance threshold from the position), a missing region of the vessel of the tibia may be selected. In some embodiments, a y coordinate for the missing region of the vessel of the tibia may be selected as small as possible (e.g., a position including a minimum y coordinate near the missing region of the vessel of the tibia is selected along the direction from the front to the rear of a subject), and the corresponding z coordinate may be selected as large as possible (e.g., a position including a minimum z coordinate near the missing region of the vessel of the tibia is selected along the direction from the foot to the knee of the measured subject). According to such a selecting way, if two missing regions of the vessel of the tibia are selected at the left leg and the right leg respectively, the regions may be data supplement regions of the vessel of the tibia.

In 1003, the first vessel generation sub-unit 901 may obtain supplement points of one or more vessel data at a data supplement region, based on the image data (e.g., the image data of the crus site obtained in 611). In some embodiments, a source distance field may be made to reach a primary part of the vessel, and pixels (or voxels) where the primary part of the vessel is reached may be set as a data supplement point in a data supplement region. For example, the data supplement point may include a start point, an end point, and a path point of a vessel.

In 1004, based on the data supplement point obtained in 1003, the first vessel generation sub-unit 901 may supplement data representing the center line of the vessel in the broken vessel data. In some embodiments, data of the center line of a vessel may be obtained based on single-source shortest path algorithms. The single-source shortest path algorithms for obtaining the center line of the vessel may include a Dijkstra algorithm, a Bellman-Ford algorithm, an A* searching algorithm, a Floyd-Warshall algorithm, a Johnson algorithm, a Viterbi algorithm, or the like. Taking the Dijkstra algorithm as an example, the value function in this algorithm may be derived from the distance transformation of the supplement region and the distance between data supplement points.

In 1005, the first vessel generation sub-unit 901 may supplement other vessel data based on the data of the center line of the vessel obtained in 1004. In some embodiments, the first vessel generation sub-unit 901 may select a certain region, outward with the center line of the vessel as a center, as a region of the vessel to be segmented, the center line may be set as a preliminary segmentation result, and the boundary values of the vessel in the original image and at least one characteristic image may be defined as vessel model conditions. In some embodiments, the characteristic image may refer to a processed image based on the original image. The process may include image transformation, image enhancement, image characteristic extraction, or the like, or a combination thereof. In some embodiments, the image characteristics may include color characteristics, texture characteristics, shape characteristics, spatial relation characteristics, or the like, or a combination thereof. Regarding a point in the data of the center line of the vessel obtained in 1004 as the seed point, and the vessel may be identified or extracted by judging that whether a value of an angiogram image of a point near the seed point satisfies the boundary value of the current vessel model condition.

FIG. 10-B is a flowchart illustrating an exemplary process for supplementing foot vessel data according to some embodiments of the present disclosure. Supplementing the foot vessel data may be performed by the second vessel generation sub-unit 902. In 1011, the second vessel generation sub-unit 902 may identify the missing data point representing the vessel of the foot in the broken vessel data.

In 1012, the second vessel generation sub-unit 902 may determine a data supplement region based on the data missing site representing the vessel of the foot obtained in 1011. In some embodiments, the second vessel generation sub-unit 902 may determine ½ of the data missing points where the foot may be located in the image data (e.g., the image data of the crus site obtained in 611) as data supplement regions.

In 1013, the second vessel generation sub-unit 902 may rank the data supplement regions obtained in 1012. For example, the second vessel generation sub-unit 902 may rank the data supplement regions obtained in 1012 in descending order of the average values of the coordinates in the z-direction (e.g., along the direction from the foot to the knee of a subject: the closer to the foot, the smaller the z coordinate is; the closer to the knee, the larger the z coordinate is).

In 1014, the second vessel generation sub-unit 902 may perform a supplement operation on the data supplement region based on the rank in 1013. In some embodiments, the higher average value of the z coordinates in the data supplement region is, the higher priority of the supplement operation is; the lower average value of the z coordinates in the data supplement region is, the lower priority of the supplement operation is. The average value of the z coordinates may refer to an average value of z-direction coordinates of multiple pixels (or voxels) in a data supplement region.

FIG. 10-C is a flowchart illustrating an exemplary process for performing a supplement operation on a data supplement region according to some embodiments of the present disclosure. In 1021, the second vessel generation sub-unit 902 may obtain a series of supplement points at a data supplement region, based on the image data (e.g., the image data of the crus site obtained in 611).

In 1022, the second vessel generation sub-unit 902 may supplement data representing the center line of the vessel in the broken vessel data, based on the data supplement points obtained in 1021. In some embodiments, the data of the center line of the vessel may be obtained based on single-source shortest path algorithms. The single-source shortest path algorithms for obtaining the center line of the vessel may include a Dijkstra algorithm, a Bellman-Ford algorithm, an A* searching algorithm, a Floyd-Warshall algorithm, a Johnson algorithm, a Viterbi algorithm, etc. Taking the Dijkstra algorithm as an example, the value function in this algorithm may be derived from the distance transformation of the supplement region and the distance between data supplement points.

In 1023, the second vessel generation sub-unit 902 may supplement other vessel data based on the data of the center line of the vessel obtained in 1022. In some embodiments, the second vessel generation sub-unit 902 may select a region, outward with the center line of the vessel as a center, as a region of the vessel to be segmented, the center line may be determined as a preliminary segmentation result, and the boundary value of the vessel in the original image and at least one characteristic image may be defined as vessel model conditions. In some embodiments, the characteristic image may refer to the processed image based on the original image. The process may include image transformation, image enhancement, image characteristic extraction, or the like, or a combination thereof. In some embodiments, the image characteristics may include color characteristics, texture characteristics, shape characteristics, spatial relation characteristics, or the like, or a combination thereof. Regarding a point in the data of the center line of the vessel obtained in 1022 as the seed point, and the vessel may be identified or extracted by judging that whether a value of an angiogram image of a point near the seed point satisfies the boundary value of the current vessel model condition.

FIG. 10-D is a flowchart illustrating an exemplary process for supplementing ilium vessel data according to some embodiments of the present disclosure. Supplementing the ilium vessel data may be performed by the third vessel generation sub-unit 903. In 1031, the third vessel generation sub-unit 903 may position the ilium segment in the image based on the obtained image data (e.g., the image data of the lower limb obtained in 611). Then, the region where the ilium segment is positioned may be preprocessed. In some embodiments, the third vessel generation sub-unit 903 may leave a blank for several middle layers of the positioned ilium segment and may expand the topmost layers (e.g., 1 to m layers) and the lowermost layers (e.g., 1 to n layers) of the ilium segment outward in the x-direction (e.g., along the direction from the right ilium to the left ilium of a subject) for attaining a point with a first gray-scale value smaller than a threshold (e.g., 100). The expanded ilium segment may be set as a region where the vessel cannot grow in 1035 (i.e., a growth control data set) to prevent the center line of the vessel grown in 1035 from passing through the ilium.

In 1032, the third vessel generation sub-unit 903 may identify the data missing point representing the vessel of the foot in the broken vessel data.

In 1033, the third vessel generation sub-unit 903 may set data supplement regions based on the data missing site representing the vessel of the ilium obtained in 1012. In some embodiments, the third vessel generation sub-unit 903 may set the broken vessel data near the range (e.g., a region within a spatial distance threshold from the y coordinate) of the y-direction coordinate where the ilium may be located (e.g., along the direction from the front to the rear of a subject, the closer to the front, the smaller the y coordinate is; the closer to the rear, the larger the y coordinate is) as data supplement regions, so that selection of crush bones near the vertebra may be avoided or decreased.

In 1034, the third vessel generation sub-unit 903 may rank the data supplement regions obtained in 1033. For example, the third vessel generation sub-unit 903 may assign a higher weight to a data supplement region where the x coordinate (e.g., along the direction from the right ilium to the left ilium of a subject: the closer to the right ilium, the smaller the x coordinate is) is closer to the center, the y coordinate (e.g., along the direction from the front to the rear of a subject: the closer to the front, the smaller the y coordinate is; the closer to the rear, the larger the y coordinate is) is lager, and obtain a value on the basis of which a ranking in the descending order may be performed to determine the rank of each data supplement region. The average value of x coordinates may refer to an average value of x-direction coordinates of multiple pixels (or voxels) in the data supplement region. The average value of the y coordinates may refer to an average value of y-direction coordinates of multiple pixels (or voxels) in the data supplement region. The rank of data supplement regions may refer to the order of supplementing data in the course of data supplementation.

In 1035, the third vessel generation sub-unit 903 may perform the supplement operation on the data supplement region based on the order ranked in 1034. The supplementation method may perform the supplement operation on the data supplement region as shown in FIG. 10-C.

FIG. 10-E is a flowchart illustrating an exemplary process for generating a vessel according to some embodiments of the present disclosure. The process for generating the vessel may include determining a value of a boundary distance field 1041, extracting a center line of a vessel 1042, and obtaining a vessel extraction result 1043. The vessel may be generated by the fourth vessel generation sub-unit 904. It should be noted that the generation of the vessel of the tibia, the vessel of the foot, and/or the vessel of the ilium may also use the process as shown in FIG. 10-E.

In 1041, a value of a boundary distance field of the pixels/voxels of the connected domain in the second subtraction image may be determined. The computing methods of the value of the boundary distance field value may be described above. In some embodiments, the fourth vessel generation sub-unit 904 may determine one or more connected domains in the second subtraction image based on the value of the boundary distance field value.

In 1042, the center line of the vessel may be extracted. In some embodiments, the fourth vessel generation sub-unit 904 may extract the center line of the vessel based on the value of the boundary distance field determined in 1041 and the shortest path algorithms. In some embodiments, the fourth vessel generation sub-unit 904 may determine growing points of one or more center lines of the vessel based on the value of the boundary distance field for extracting the center line of the vessel based on the growing point. For example, the fourth vessel generation sub-unit 904 may obtain a first vessel growing point and a second vessel growing point based on the value of the boundary distance field, and extract the center line of the vessel by using the shortest path algorithms, based on the first vessel growing point and the second vessel growing point. In some embodiments, the fourth vessel generation sub-unit 904 may exclude the skeleton region in the second skeleton mask to extract the center line of the vessel. This means that the skeleton region in the second skeleton mask may be bypassed in the process of extracting the center line of the vessel. This means that the extracted center line of the vessel may not pass through the skeleton region. The shortest path algorithm may include a Dijkstra algorithm, a Bellman-Ford algorithm, an A* searching algorithm, a Floyd-Warshall algorithm, a Johnson algorithm, a Viterbi algorithm, or the like, or a combination thereof.

In 1043, the vessel may be generated based on the center line of the vessel to obtain an extraction result of the vessel. In some embodiments, the fourth vessel generation sub-unit 904 may select one or more pixels/voxels in the center line of the vessel as the seed point(s). In some embodiments, the regional growth may be performed based on the seed point to obtain the extraction result of the vessel. Similar to 1042, the vessel growth may bypass the skeleton region.

Figure 11:
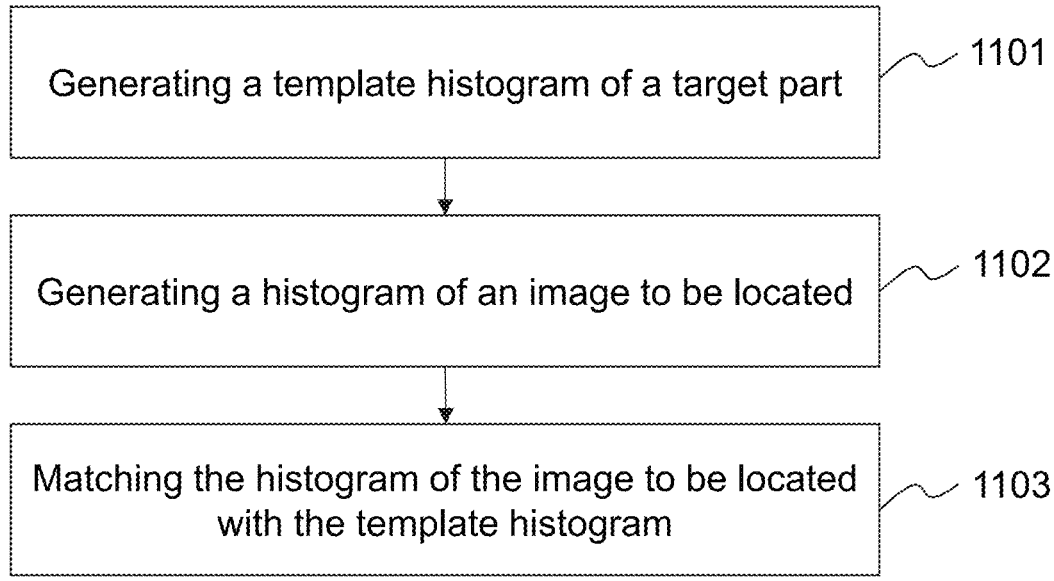
FIG. 11 is a flowchart illustrating an exemplary process for positioning a specific site of a human body in a medicine image according to some embodiments of the present disclosure.

FIG. 11 is a flowchart illustrating an exemplary process for positioning a specific site of a human body in a medicine image according to some embodiments of the present disclosure. The method may achieve positioning by comparing some characteristics of each layer in a data set of a template image and in a data set of an image to be positioned.

In 1101, the data processing system 130 may generate a template image representing a target site. In some embodiments, the template image may include one or more template histograms. In a template image, some characteristics, for example, $f_i$, $i \in n$ may be extracted for a layer where the identified position may be located, and each characteristic may be formed as a template histogram $T_i$, $i \in n$ along the z-direction. The template image may refer to an image including a region where the target site may be located. For example, if what is to be positioned is an ilium, the template image may include an image of a region where the ilium may be located. In some embodiments, the template image and the image to be positioned may come from different measured subjects. The characteristics may include the number of pixels (or voxels) in a certain gray scale range, the sectional area of the bone, or the like, or a combination thereof. The selected characteristics may include certain invariance. The invariance may refer that the difference among the characteristics of different measured subjects is small (e.g., the difference may be within a certain threshold range). For example, since every tissue in the CT angiographic image includes a specific gray-scale value, the number of pixels (or voxels) in certain gray scales range in each layer may include certain invariance for different measured subjects. In some embodiments, the data processing system 130 may generate a template image based on a reference image. The reference image may include image data similar to those of the sites of the measured subject in the image to be positioned. Specifically, the data process system 130 may obtain reference image data, extract characteristics of the reference image data, and generate a template image based on the characteristics.

In 1102, the data processing system 130 may obtain the image to be positioned, extract one or more characteristics identical to the characteristics in 1101 for each layer, and generate an image histogram $h_i$, i∈n to be positioned for each characteristic along the z direction (e.g., along the direction from the foot to the head of the subject: the closer to the foot, the smaller the z coordinate is; the closer to the head, the larger the z coordinate is).

In 1103, the data processing system 130 may compare the image histogram to be positioned with the template histogram. For each characteristic, the corresponding template histogram $T_i$ may be positioned above the $h_i$ to perform moving comparison; every time when the template histogram is moved to a position, the template histogram $T_i$ may be stretched and the similarity degree of the image histogram to be positioned and the template histogram may be calculated, based on the corresponding local maximum values and the corresponding local minimum values. The position with a maximum similarity degree is the position of the site to be positioned. The similarity degree may be calculated based on the difference between the characteristics of the position where the image histogram to be positioned and the template histogram may be overlapped. For example, the sum of the absolute values of characteristic difference values of a position may be divided by the zoom factor of the template to obtain the local similarity degree corresponding to the characteristic. Further, the sum of local similarity degrees corresponding to two or more characteristics may be designated as a total local similarity degree, so that a position including the maximum total local similarity degree may be designated as a position where the specific site may be positioned.

EXAMPLES

The following embodiments are for illustration purposes and are not intended to limit the scope of the present disclosure as set forth in the embodiments.

Example 1

Figure 12:
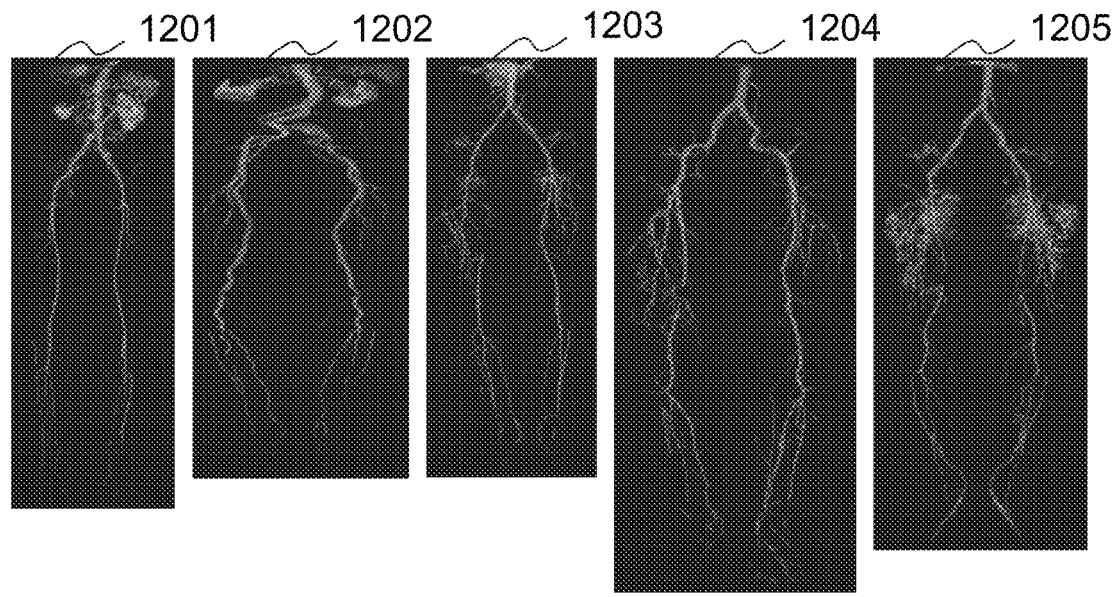
FIG. 12 is a schematic diagram illustrating exemplary results of five vessels of lower limbs according to some embodiments of the present disclosure.

FIG. 12 is a schematic diagram illustrating exemplary results of five vessels of lower limbs according to some embodiments of the present disclosure. A first lower limb vessel 1201, a second lower limb vessel 1202, a third lower limb vessel 1203, a fourth lower limb vessel 1204, and a fifth lower limb vessel 1205 were obtained from image data of five different human subjects. In the process for extracting the vessels of the lower limbs shown in FIG. 12, processes of skeleton extraction, broken vessel segment extraction, and vessel generation (e.g., the method shown in FIG. 6-B) were used, and different parameters were used in the specific process operation. A vessel generation technique (e.g., the processes shown in FIGS. 10-A, 10-B, and 10-C) were used in some sites (e.g., a crus, an ilium, or a foot bone).

Example 2

Figure 13:
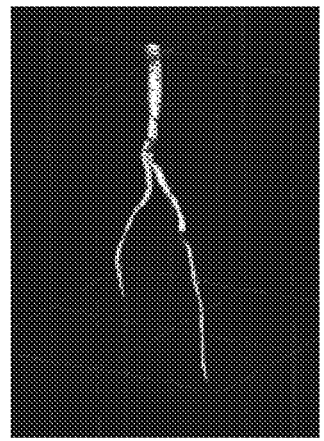
FIG. 13 is a schematic diagram illustrating an exemplary second vessel mask according to some embodiments of the present disclosure.

FIG. 13 is a schematic diagram illustrating an exemplary second vessel mask according to some embodiments of the present disclosure. The second vessel mask is the result obtained according to the process shown in FIG. 7-E. As shown in FIG. 13, the second vessel mask may include most of the vascular tissues.

Example 3

Figure 14:
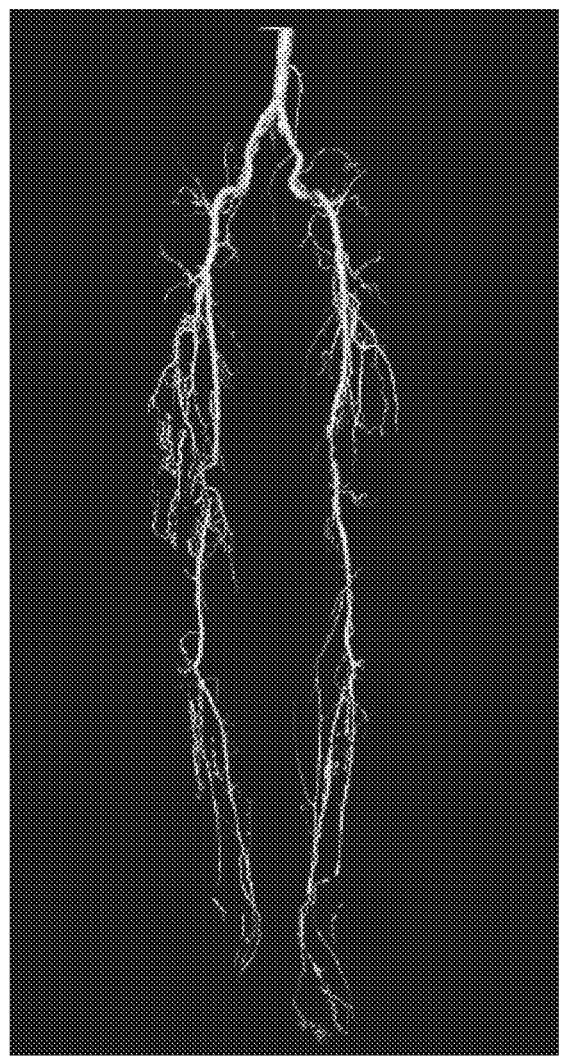
FIG. 14 is a schematic diagram illustrating an exemplary result of vessel extraction according to some embodiments of the present disclosure.

FIG. 14 is a schematic diagram illustrating an exemplary result of vessel extraction according to some embodiments of the present disclosure. The vessel shown in FIG. 14 is the result obtained according to the process shown in FIG. 10-E.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (e.g., through the Internet using an Internet Service Provider) or in a cloud computing environment or offered as a service such as a software as a service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:
1. A method, comprising:
obtaining an original image including a plurality of image data, each of the plurality of image data corresponding to a pixel (or a voxel), the plurality of image data including a target data set, the target data set representing a first structure;
extracting a first reference data set from the plurality of image data, the first reference data set including the target data set;
extracting a second reference data set from the plurality of image data, the second reference data set including data of a second structure;
obtaining a vessel mask corresponding to the first structure;
determining a first subtraction image corresponding to the second structure based on the first reference data set and the vessel mask;
determining, based on the first subtraction image, a first seed point corresponding to the second structure;
determining a first mask by performing, based on the first seed point, a regional growth on the first subtraction image, wherein the first mask is a first skeleton mask and the extracting the second reference data set comprises:
segmenting the second structure based on the first subtraction image to obtain the first skeleton mask; and
obtaining a second skeleton mask based on the original image and the first skeleton mask, wherein pixels or voxels in the second skeleton mask and data in the second reference data set are bijective; and
obtaining the target data set based on the first mask, the first reference data set, and the second reference data set, the obtaining the target data set comprising:
obtaining a frame data set based on the first reference data set and the second reference data set, the frame data set being a subset of the target data set, wherein the obtaining the frame data set comprises:
subtracting the second skeleton mask from a first image to obtain a second subtraction image, wherein pixels or voxels in the second subtraction image and data in the frame data set are bijective; and performing at least one data supplement operation on the frame data set to obtain the target data set.

2. The method of claim 1, wherein the first structure includes a vessel, the second structure includes a skeleton, the target data set includes vessel data, the first reference data set includes vessel data and skeleton data, the second reference data set includes skeleton data, and the frame data set includes data of broken vessel segments.

3. The method of claim 2, the performing at least one data supplement operation on the frame data set comprising:
   selecting a third seed point from the frame data set; and
   performing a regional growth based on a second threshold and the third seed point to obtain the target data set.

4. The method of claim 1, the extracting the first reference data set comprising:
   determining at least one connected domain CD1 in the original image;
   determining a second seed point based on the at least one connected domain CD1; and
   performing a regional growth on the original image based on the second seed point and a first threshold to obtain the first image, wherein pixels or voxels in the first image and data in the first reference data set are bijective.

5. The method of claim 4, the determining the second seed point comprising:
   determining values of a boundary distance field of the at least one connected domain CD1 to obtain a data set pfield-1;
   determining a circularity degree of the at least one connected domain CD1 based on the data set pfield-1;
   determining a target connected domain based on the at least one connected domain CD1; and
   determining the second seed point based on the target connected domain.

6. The method of claim 5, the determining the circularity degree of the at least one connected domain CD1 comprising:
   determining a radius of the at least one connected domain CD1 based on the data set pfield-1;
   determining a circular area of the at least one connected domain CD1 based on the radius of the at least one connected domain CD1; and
   determining the circularity degree of the at least one connected domain CD1 based on the circular area of the at least one connected domain CD1 and an actual area of the at least one connected domain CD1.

7. The method of claim 4, wherein the obtaining the vessel mask corresponding to the first structure comprising:
   performing a regional growth on the first image based on the second seed point to obtain a first vessel mask; and
   dilating the first vessel mask to obtain the vessel mask.

8. The method of claim 1, wherein the first seed point is a skeleton seed point, and the determining, based on the first subtraction image, the first seed point corresponding to the second structure comprises:
   calculating a boundary distance field based on the first subtraction image to obtain a data set pfiled-3;
   determining the skeleton seed point based on the data set pfield-3.

9. The method of claim 1, the obtaining the second skeleton mask comprising:
   determining a first skeleton region based on the first skeleton mask; and
   dilating the first skeleton region to obtain a first temporary skeleton mask.

10. The method of claim 9, the obtaining the second skeleton mask further comprising:
    performing a regional growth on the original image based on a second threshold to obtain a second image;
    filling the second image to obtain a filled second image;
    obtaining a superimposition image based on the first temporary skeleton mask and the filled second image; and
    performing a closing operation on at least one connected domain CD2 in the superimposition image to obtain the second skeleton mask.

11. The method of claim 9, the determining the first skeleton region comprising:
    eroding the first skeleton mask to obtain at least one connected domain CD3; and
    determining the first skeleton region based on the at least one connected domain CD3.

12. The method of claim 11, the determining the first skeleton region further comprising:
    designating a connected domain with the maximum area or the maximum volume in the at least one connected domain CD3 as the first skeleton area.

13. The method of claim 1; the performing at least one data supplement operation on the frame data set comprising:
    extracting a center line of a vessel based on the second subtraction image; and
    generating the vessel based on the center line of the vessel.

14. The method of claim 13, the extracting the center line of the vessel comprising:
    calculating a boundary distance field based on the second subtraction image;
    obtaining a first vessel growing point and a second vessel growing point based on the boundary distance field; and
    extracting the center line of the vessel using a shortest route algorithm based on the first vessel growing point and the second vessel growing point.

15. The method of claim 14, the extracting the center line of the vessel further comprising:
    determining a second skeleton region in the second skeleton mask; and
    extracting the center line of the vessel by excluding the second skeleton region.

16. A non-transitory computer readable medium including executable instructions that, when executed by at least one processor, cause the at least one processor to effectuate a method comprising:
    obtaining an image including a plurality of image data, each of the plurality of image data corresponding to a pixel (or a voxel), the plurality of image data including a target data set, the target data set representing a first structure;
    extracting a first reference data set from the plurality of image data, the first reference data set including the target data set;
    extracting a second reference data set from the plurality of image data, the second reference data set including data of a second structure;
    obtaining a vessel mask corresponding to the first structure;
    determining a first subtraction image corresponding to the second structure based on the first reference data set and the vessel mask;
    determining, based on the first subtraction image, a first seed point corresponding to the second structure;

determining a first mask by performing, based on the first seed point, a regional growth on the first subtraction image, wherein the first mask is a first skeleton mask and the extracting the second reference data set comprises:
  segmenting the second structure based on the first subtraction image to obtain the first skeleton mask; and
  obtaining a second skeleton mask based on the original image and the first skeleton mask, wherein pixels or voxels in the second skeleton mask and data in the second reference data set are bijective; and
obtaining the target data set based on the first mark, the first reference data set, and the second reference data set, the obtaining the target data set comprising:
  obtaining a frame data set based on the first reference data set and the second reference data set, the frame data set being a subset of the target data set, wherein the obtaining the frame data set comprises:
    subtracting the second skeleton mask from a first image to obtain a second subtraction image, wherein pixels or voxels in the second subtraction image and data in the frame data set are bijective; and
  performing at least one data supplement operation on the frame data set to obtain the target data set.

17. A system comprising:
at least one processor; and
executable instructions that, when executed by the at least one processor, causes the at least one processor to effectuate a method comprising:
  obtaining an original image including a plurality of image data, each of the plurality of image data corresponding to a pixel (or a voxel), the plurality of image data including a target data set, the target data set representing a first structure;
  extracting a first reference data set from the plurality of image data, the first reference data set including the target data set;
  extracting a second reference data set from the plurality of image data;
  obtaining a vessel mask corresponding to the first structure;
  determining a first subtraction image corresponding to the second structure based on the first reference data set and the vessel mask;
  determining, based on the first subtraction image, a first seed point corresponding to the second structure;
  determining a first mask by performing, based on the first eed point, a regional growth on the first subtraction image, wherein the first mask is a first skeleton mask and the extracting the second reference data set comprises:
    segmenting the second structure based on the first subtraction image to obtain the first skeleton mask;
    obtaining a second skeleton mask based on the original image and the first skeleton mask, wherein pixels or voxels in the second skeleton mask and data in the second reference data set are bijective; and
  obtaining the target data set based on the first mark, the first reference data set, and the second reference data set, the obtaining the target data set comprising:
    obtaining a frame data set based on the first reference data set and the second reference data set, the frame data set being a subset of the target data set, wherein the obtaining the frame data set comprises:
      subtracting the second skeleton mask from a first image to obtain a second subtraction image wherein pixels or voxels in the second subtraction image and data in the frame data set are bijective; and
    performing at least one data supplement operation on the frame data set to obtain the target data set.

* * * * *